US012133669B2

(12) United States Patent
Rosen et al.

(10) Patent No.: US 12,133,669 B2
(45) Date of Patent: Nov. 5, 2024

(54) AUTOMATED DERMATOLOGICAL CRYOSPRAY TREATMENT PLANNING SYSTEM

(71) Applicant: R2 Technologies, Inc., San Ramon, CA (US)

(72) Inventors: Jesse Rosen, Albany, CA (US); Erica Elford, San Mateo, CA (US); Dylan McReynolds, Berkeley, CA (US); Erik Stauber, Albany, CA (US)

(73) Assignee: R2 Technologies, Inc., San Ramon, CA (US)

( * ) Notice: Subject to any disclaimer, the term of this patent is extended or adjusted under 35 U.S.C. 154(b) by 510 days.

(21) Appl. No.: 16/723,859

(22) Filed: Dec. 20, 2019

(65) Prior Publication Data
US 2020/0214757 A1   Jul. 9, 2020

Related U.S. Application Data

(60) Provisional application No. 62/784,124, filed on Dec. 21, 2018.

(51) Int. Cl.
*A61B 18/02* (2006.01)
*A61B 5/00* (2006.01)
(Continued)

(52) U.S. Cl.
CPC .......... *A61B 18/0218* (2013.01); *A61B 5/441* (2013.01); *A61B 34/20* (2016.02);
(Continued)

(58) Field of Classification Search
CPC . A61B 2018/0218; A61B 5/441; A61B 34/20; A61B 2018/00714;
(Continued)

(56) References Cited

U.S. PATENT DOCUMENTS 3,664,344 A   5/1972   Bryne
4,206,609 A   6/1980   Durenec et al.
(Continued)

FOREIGN PATENT DOCUMENTS

CN   101778650 A   7/2010
CN   104720960 A   6/2015
(Continued)

OTHER PUBLICATIONS

Andrews, Cryosurgery For Common Skin Conditions, American Family Physician, vol. 69, Issue 10, May 15, 2004, pp. 2365-2372.
(Continued)

*Primary Examiner* — Joseph A Stoklosa
*Assistant Examiner* — Annie L Shoulders
(74) *Attorney, Agent, or Firm* — Kilpatrick Townsend & Stockton LLP

(57) ABSTRACT

The present is directed to improved systems, methods, and devices for providing skin cooling treatment. The skin cooling treatment system can include a mechanical arm and a cryospray applicator coupled to a distal end of the mechanical arm. The skin cooling treatment system can include a processor that can receive imagery of a portion of skin of a patient for receiving a skin cooling treatment and automatically identify boundaries from the received imagery to designate portions of the skin of the patient for receiving the skin cooling treatment. The processor can determine an instantaneous treatment footprint and can generate a treatment path based on the treatment footprint. The processor can control the cryospray applicator to deliver the skin cooling treatment to the skin according to the treatment path.

37 Claims, 10 Drawing Sheets

(51) Int. Cl.
  *A61B 18/00* (2006.01)
  *A61B 34/20* (2016.01)
  *G16H 20/40* (2018.01)

(52) U.S. Cl.
  CPC ...... *G16H 20/40* (2018.01); *A61B 2018/0047* (2013.01); *A61B 2018/00714* (2013.01); *A61B 2018/00791* (2013.01); *A61B 2034/2065* (2016.02)

(58) Field of Classification Search
  CPC .. A61B 2018/00791; A61B 2034/2065; G16H 20/40
  See application file for complete search history.

(56) References Cited

U.S. PATENT DOCUMENTS

| | | |
|---|---|---|
| 4,946,460 A | 8/1990 | Merry et al. |
| 5,531,742 A | 7/1996 | Barken |
| 5,596,875 A | 1/1997 | Berry et al. |
| 5,759,182 A | 6/1998 | Varney et al. |
| 5,848,981 A | 12/1998 | Herbranson |
| 5,901,707 A | 5/1999 | Goncalves |
| 6,017,337 A | 1/2000 | Pira |
| 6,139,544 A | 10/2000 | Mikus et al. |
| 6,226,996 B1 | 5/2001 | Weber et al. |
| 6,235,018 B1 | 5/2001 | LePivert |
| 6,413,252 B1 | 7/2002 | Zavislan |
| 6,430,956 B1 | 8/2002 | Haas et al. |
| 6,503,246 B1 | 1/2003 | Har-shai et al. |
| 6,629,417 B2 | 10/2003 | Haas et al. |
| 6,669,688 B2 | 12/2003 | Svaasand et al. |
| 6,960,202 B2 | 11/2005 | Cluzeau et al. |
| 6,981,970 B2 | 1/2006 | Karni |
| 7,367,341 B2 | 5/2008 | Anderson et al. |
| 7,422,576 B2 | 9/2008 | Boynton et al. |
| 7,630,774 B2 | 12/2009 | Karni et al. |
| 7,751,452 B2 | 7/2010 | Vogler |
| 7,780,656 B2 | 8/2010 | Tankovich |
| 7,824,395 B2 | 11/2010 | Chan et al. |
| 7,850,683 B2 | 12/2010 | Elkins et al. |
| 7,962,192 B2 | 6/2011 | Bodduluri et al. |
| 7,963,959 B2 | 6/2011 | Da Silva et al. |
| 8,150,532 B2 | 4/2012 | Karni et al. |
| 8,308,717 B2 | 11/2012 | Rapoport |
| 8,435,194 B2 | 5/2013 | Dverin et al. |
| 8,562,597 B2 | 10/2013 | Van Der Heijden et al. |
| 8,579,835 B2 | 11/2013 | Britva et al. |
| 8,764,701 B1 | 7/2014 | Hicks |
| 8,769,733 B2 | 7/2014 | Galyean et al. |
| 8,950,406 B2 | 2/2015 | Karni et al. |
| 9,050,117 B2 | 6/2015 | Nelson et al. |
| 9,241,753 B2 | 1/2016 | Fourkas et al. |
| 9,326,808 B2 | 5/2016 | Damasco et al. |
| 9,522,031 B2 | 12/2016 | Anderson et al. |
| 9,545,284 B2 | 1/2017 | Karni |
| 9,549,773 B2 | 1/2017 | Anderson et al. |
| 9,597,528 B2 | 3/2017 | Schomacker et al. |
| 9,675,419 B2 | 6/2017 | Akeel et al. |
| 9,724,150 B2 | 8/2017 | Bao et al. |
| 9,974,684 B2 | 5/2018 | Anderson et al. |
| 10,118,051 B2 | 11/2018 | Taghizadeh |
| 10,299,871 B2 | 5/2019 | Zingaretti et al. |
| 10,349,997 B1 | 7/2019 | O'Reilly |
| 2003/0100936 A1 | 5/2003 | Altshuler et al. |
| 2004/0167592 A1 | 8/2004 | Grove et al. |
| 2005/0222565 A1 | 10/2005 | Manstein |
| 2006/0058238 A1 | 3/2006 | Laurent-Applegate et al. |
| 2006/0155267 A1 | 7/2006 | Berzak et al. |
| 2006/0189976 A1 | 8/2006 | Karni et al. |
| 2006/0206103 A1 | 9/2006 | Altshuler et al. |
| 2006/0282067 A1 | 12/2006 | Koop et al. |
| 2007/0088386 A1 | 4/2007 | Babaev |
| 2007/0129714 A1 | 6/2007 | Elkins et al. |
| 2007/0135876 A1 | 6/2007 | Weber |
| 2007/0185527 A1 | 8/2007 | Babaev |
| 2008/0039747 A1 | 2/2008 | Baerwalde et al. |
| 2008/0071332 A1 | 3/2008 | Nelson et al. |
| 2008/0119828 A1 | 5/2008 | Nelson et al. |
| 2008/0119839 A1 | 5/2008 | Vancelette |
| 2008/0183164 A1 | 7/2008 | Elkins et al. |
| 2008/0183167 A1 | 7/2008 | Britva et al. |
| 2008/0287943 A1 | 11/2008 | Weber et al. |
| 2009/0012585 A1 | 1/2009 | Karni et al. |
| 2009/0171424 A1 | 7/2009 | Britva et al. |
| 2009/0281537 A1 | 11/2009 | Britva et al. |
| 2010/0036295 A1 | 2/2010 | Altshuler et al. |
| 2010/0087806 A1* | 4/2010 | Da Silva ............ A61B 18/0218 606/22 |
| 2010/0114007 A1 | 5/2010 | Fischer et al. |
| 2011/0162390 A1 | 7/2011 | Littrup et al. |
| 2011/0313411 A1 | 12/2011 | Anderson et al. |
| 2012/0041525 A1 | 2/2012 | Karni |
| 2012/0071794 A1 | 3/2012 | Karni |
| 2012/0123319 A1 | 5/2012 | Britva et al. |
| 2012/0330194 A1 | 12/2012 | Britva et al. |
| 2013/0296812 A1* | 11/2013 | Bangera ................ B05B 12/124 604/290 |
| 2014/0007895 A1 | 1/2014 | Britva et al. |
| 2014/0135662 A1 | 5/2014 | Britva et al. |
| 2014/0303696 A1 | 10/2014 | Anderson et al. |
| 2014/0303697 A1 | 10/2014 | Anderson et al. |
| 2015/0045857 A1 | 2/2015 | Britva et al. |
| 2015/0080991 A1 | 3/2015 | Britva et al. |
| 2015/0216720 A1 | 8/2015 | DeBenedictis et al. |
| 2015/0223975 A1 | 8/2015 | Anderson et al. |
| 2016/0051401 A1 | 2/2016 | Yee et al. |
| 2016/0135985 A1 | 5/2016 | Anderson et al. |
| 2016/0157915 A1 | 6/2016 | Anderson et al. |
| 2017/0020636 A1 | 1/2017 | Akeel et al. |
| 2017/0065323 A1 | 3/2017 | Rosen et al. |
| 2017/0231721 A1 | 8/2017 | Akeel et al. |
| 2017/0325992 A1* | 11/2017 | DeBenedictis ........ A61F 7/0085 |
| 2017/0326346 A1* | 11/2017 | Jimenez Lozano ..... A61F 7/007 |
| 2017/0348143 A1 | 12/2017 | Rosen et al. |
| 2018/0028253 A1 | 2/2018 | Anderson et al. |
| 2018/0271597 A1* | 9/2018 | Eisenmann .......... A61N 5/0616 |
| 2018/0344411 A1* | 12/2018 | Fahey .................... A61B 34/20 |
| 2018/0360520 A1 | 12/2018 | Avalle |
| 2019/0047145 A1 | 2/2019 | Akeel et al. |
| 2019/0239938 A1 | 8/2019 | Kazic et al. |

FOREIGN PATENT DOCUMENTS

| | | |
|---|---|---|
| DE | 9217897 | 11/1993 |
| EP | 1797847 | 6/2007 |
| EP | 2201917 | 6/2010 |
| EP | 2272455 | 1/2011 |
| GB | 2286660 | 8/1995 |
| JP | H04133822 A | 5/1992 |
| JP | 10052475 | 2/1998 |
| JP | 2005237908 | 9/2005 |
| JP | 2014208309 A | 11/2014 |
| KR | 200431404 | 11/2006 |
| KR | 100802155 | 2/2008 |
| RU | 2074680 | 3/1997 |
| WO | 2003/078596 A2 | 9/2003 |
| WO | 2003/078596 A3 | 9/2003 |
| WO | 2005/096979 | 10/2005 |
| WO | 2006/066226 | 6/2006 |
| WO | 2006/127467 | 11/2006 |
| WO | 2007/064718 | 6/2007 |
| WO | 2008/055243 | 5/2008 |
| WO | 2008/083305 | 7/2008 |
| WO | 2008/091983 | 7/2008 |
| WO | 2009/146053 | 12/2009 |
| WO | 2010/017477 | 2/2010 |
| WO | 2013/075006 | 5/2013 |
| WO | 2013/075016 | 5/2013 |
| WO | 2016/022347 A1 | 2/2016 |
| WO | 2017/041022 | 3/2017 |
| WO | 2017/181156 A1 | 10/2017 |

(56) References Cited

FOREIGN PATENT DOCUMENTS

WO   2018/093964 A1   5/2018
WO   2019/089995 A1   5/2019

OTHER PUBLICATIONS

Gage et al., Critical Temperature for Skin Necrosis in Experimental Cryosurgery, Cryobiology, vol. 19, 1982, pp. 273-282.
Gage et al., Sensitivity of Pigmented Mucosa and Skin to Freezing Injury, Cryobilogy, vol. 16, 1979, pp. 348-361.
Har-Shai et al., Effect of Skin Surface Temperature on Skin Pigmentation During Contact and Intralesional Cryosurgery of Hypertrophic Scars and Kleoids, Journal of the European Academy of Dermatology and Venereology, vol. 21, No. 2, Feb. 2007, pp. 191-198.
Thai et al., Cryosurgery of Benign Skin Lesions, Australasian Journal of Dermatology, vol. 40, 1999, pp. 175-186.
Yeh, Cryosurgical Treatment of Melanin-Pigmented Gingiva, Oral Surgery, Oral Medicine, Oral Pathology, Oral Radiology, and Endodontology, vol. 86, Issue 6, Jun. 1998, pp. 660-663.
Zachariassen et al., Ice Nucleation and Antinucleation in Nature, Cryobiology, vol. 41, Issue 4, Dec. 2000, pp. 257-279.

\* cited by examiner

AUTOMATED DERMATOLOGICAL CRYOSPRAY TREATMENT PLANNING SYSTEM

CROSS-REFERENCES TO RELATED APPLICATIONS

The present application claims the benefit of priority of U.S. Provisional Application No. 62/784,124 filed on Dec. 21, 2018; the entirety of which is hereby incorporated by reference herein.

BACKGROUND OF THE INVENTION

Cryotherapy is the local or general use of cold in medical therapy. Cryotherapy can include the controlled freezing of biological tissue, which controlled freezing of biological tissue, such as skin tissue, can produce various effects. Certain tissue freezing procedures and devices, such as conventional cryoprobes, can cause severe freezing of tissue and generate cellular and visible skin damage.

There is a demand for cosmetic products that can lighten the appearance of skin or otherwise controllably affect skin pigmentation. For example, it may be desirable to lighten the overall complexion or color of a region of skin to alter the general appearance for cosmetic reasons. Also, lightening of particular hyperpigmented regions of skin, such as freckles, 'café au lait' spots, melasma, or dark circles under the eyes that may result from excessive local amounts of pigment in the skin, may also be desirable for cosmetic reasons. Hyperpigmentation can result from a variety of factors such as UV exposure, aging, stress, trauma, inflammation, etc. Such factors can lead to an excess production of melanin, or melanogenesis, in the skin by melanocytes, which can lead to formation of hyperpigmented areas. Such hyperpigmented areas are typically associated with excess melanin within the epidermis and/or dermal-epidermis junction. However, hyperpigmentation can also result from excess melanin deposited within the dermis.

Hypopigmentation of skin tissue has been observed as a side effect in response to temporary cooling or freezing of the tissue, such as may occur during conventional cryosurgery procedures. Loss of pigmentation following skin cooling or freezing may result from decreased melanin production, decreased melanosome production, destruction of melanocytes, or inhibited transfer or regulation of melanosome into the keratinocytes in the lower region of the epidermal layer. The resultant hypopigmentation may be long-lasting or permanent. However, it has also been observed that some of these freezing procedures can generate regions of hyperpigmentation (or skin darkening) of skin tissue. The level of increase or decrease in pigmentation may be dependent upon certain aspects of the cooling or freezing conditions, including the temperature of the cooling treatment, and the length of time the tissue is maintained in a frozen state.

Improved hypopigmentation treatments, devices, and systems have been developed to improve the consistency of skin freezing and the overall hypopigmentation consistency. For example, it has been observed that moderate degrees of freezing (e.g., −4 to −30 degrees Celsius) at shorter time frames (e.g., 30 to 60 seconds) can produce particular dermatological effects, such as affecting the expression of skin pigmentation (e.g., hypopigmentation). Cryotherapy can be provided using a variety of techniques including the direct application of a cryogen spray to the skin of the patient or the application of a cooled probe or plate to the skin of the patient. Exemplary methods and devices are described in: U.S. Patent Publication No. 2011/0313411, filed on Aug. 7, 2009, and entitled "METHOD AND APPARATUS FOR DERMATOLOGICAL HYPOPIGMENTATION"; U.S. Patent Publication No. 2014/0303696, filed on Nov. 16, 2012, and entitled "METHOD AND APPARATUS FOR CRYOGENIC TREATMENT OF SKIN TISSUE"; U.S. Patent Publication No. 2014/0303697, filed on Nov. 16, 2012, and entitled "METHOD AND APPARATUS FOR CRYOGENIC TREATMENT OF SKIN TISSUE"; U.S. Patent Publication No. 2015/0223975, filed on Feb. 12, 2015, and entitled "METHOD AND APPARATUS FOR AFFECTING PIGMENTATION OF TISSUE"; U.S. Patent Publication No. 2017/0065323, filed on Sep. 6, 2016, and entitled "MEDICAL SYSTEMS, METHODS, AND DEVICES FOR HYPOPIGMENTATION COOLING TREATMENTS", the entirety of each of which is hereby incorporated by reference herein.

While the treatment of skin or a localized lesion to affect pigmentation can be accomplished with cryotherapy, it may be desirable to provide improved methods, systems, and devices for cryotherapy. In particular, improved designs, controls and parameters associated with cryogen delivery to achieve consistent and reliable skin freezing and desired skin treatment effect may be of benefit. Accordingly, improved dermatological cryospray methods, systems, and devices are desirable.

BRIEF SUMMARY OF THE INVENTION

The present invention relates to improved systems, devices, and methods for planning and delivering a cooling treatment to the skin of a patient. More specifically, the present invention relates to improved dermatological cryospray methods, devices, and systems that provide improved cooling treatments and improved consistency of skin cooling treatment results while limiting adverse side effects from such treatments. Exemplary embodiments include a mechanical arm and a cryospray applicator coupled to a distal end of the mechanical arm. The mechanical arm and the cryospray applicator can be communicatingly coupled to a processor which can receive information from a sense subsystem and/or a visualization subsystem, which subsystems can be a part of the cryospray applicator and/or can be coupled to the cryospray applicator.

The processor can receive image data of an area of the patient's skin designated for receiving a treatment. The processor can identify boundaries based on one or several anatomical features identified from the received image data. The processor can generate a treatment path which can be used to control the sweeping of the cryospray applicator over the area of the patient's skin designated for receiving treatment and/or the delivery of cooling therapy to the area of the patient's skin designated for receiving treatment. During the delivery of the treatment, the processor can continue to receive data from the sense subsystem and/or the visualization subsystem. This received data can used by the processor to affect one or several attributes of the treatment including, for example, the dosing, the distance between the cryospray applicator and the portion of skin being treated, the alignment of the cryospray application with respect to the patient's skin, and/or the sweeping of the cryospray applicator across the patient's skin. The processor can further detect movement by the patient and can adjust treatment delivery based on this detected movement. Further, the processor can receive data from the sense subsystem and/or the visualization subsystem following delivery of the cooling treatment. This information can be used by the processor to evaluate the effectiveness of the treatment and to update, for example, a patient profile of the patient receiving the treatment. This updated patient profile can be used to modify future treatments provided to the patient and/or to other patients. Through this functionality, the consistency of the treatment can be improved, and treatment effectiveness can be improved.

One aspect of the present disclosure relates to a method of controlling a skin cooling treatment system. The skin cooling system can include a mechanical arm having a cryospray applicator coupled to a distal end of the mechanical arm. The method can include receiving image data, also referred to herein as imagery, of a portion of skin of a patient for receiving a skin cooling treatment and automatically identifying boundaries from the received imagery to designate portions of the skin of the patient for receiving the skin cooling treatment. The method can include determining an instantaneous treatment footprint, generating a treatment path for the portion of skin of the patient designated for receiving the skin cooling treatment based on the treatment footprint, and delivering the skin cooling treatment to the skin according to the treatment path.

In some embodiments, receiving imagery of the portion of skin of the patient can include generating imagery of the portion of the skin of the patient with a vision system coupled to the cryospray applicator. In some embodiments, the vision system can be coupled to the distal end of the mechanical arm. In some embodiments, the imagery includes visible spectrum imagery and infrared imagery.

In some embodiments, the method includes determining perfusion of the portion of skin designated for receiving the skin cooling treatment. In some embodiments, the method includes adjusting a dosing according to the perfusion of the portion of skin designated for receiving the skin cooling treatment. In some embodiments, delivering the skin cooling treatment includes advancing the cryospray applicator across the skin of the patient according to the treatment path.

In some embodiments, the method includes receiving temperature information from the treatment footprint and changing the advancing of the cryospray applicator across the skin according to the temperature information. In some embodiments, the temperature information includes data characterizing an advance of freezing-front. In some embodiments, automatically identifying boundaries can include identifying a no-go feature, creating a no-go zone including the no-go feature and a safety offset at least partially surrounding the no-go feature, and creating boundary delineating between the no-go-zone and the portions of skin designated for receiving skin cooling treatment. In some embodiments, the treatment path prevents treatment in the no-go zone.

In some embodiments, the method includes ascertaining an attribute of the skin designated for receiving the skin cooling treatment before delivering the skin cooling treatment. In some embodiments, the attribute can be at least one of: a deformation, or a cooling response. In some embodiments, determining the attribute of the skin includes directing a spray at at least some of the skin designated for receiving the skin cooling treatment, and measuring a deformation of the at least some of the skin resulting from the directed spray.

In some embodiments, the method includes modifying the delivering of the skin cooling treatment based on the measured deformation of the at least some of the skin resulting from the directed spray. In some embodiments, the method includes selecting a nozzle. In some embodiments, the instantaneous treatment footprint is determined based on the selected nozzle. In some embodiments, the method includes determining an attribute of the treated skin subsequent to the delivering of the skin cooling treatment. In some embodiments, the attribute can be at least one of: an erythema level or a re-warming rate.

In some embodiments, the method includes delivering a rewarming treatment based on the determined attribute of the treated skin. In some embodiments, the method includes updating a patient profile of the patient with information for adjusting a future treatment based on the determined attribute of the treated skin. In some embodiments, the method includes detecting a motion of the patient, generating a modified treatment path based on the motion of the patient, and delivering the skin cooling treatment according to the modified treatment path.

One aspect of the present disclosure relates to a method of controlling a skin cooling treatment system, the skin cooling treatment system including a mechanical arm having a cryospray applicator coupled to a distal end of the mechanical arm. The method can include sweeping the cryospray applicator across a portion of skin of a patient according to received control signals, determining a distance between the portion of skin of the patient and the cryospray applicator, determining a location of the cryospray applicator with respect to the portion of skin based on received imagery, receiving dosing information, and automatically moving the cryospray applicator independent of the received control signals. In some embodiments, the cryospray applicator can be moved independent of the received control signals based on at least one of: the distance between the portion of the skin of the patient and the cryospray applicator, the location of the cryospray applicator with respect to the portion of skin, or the dosing information.

In some embodiments, automatically moving the cryospray applicator independent of the received control signals includes at least one of: changing a sweeping speed of the cryospray applicator, changing the sweeping of the cryospray applicator, or changing the distance between the portion of the skin of the patient and the cryospray applicator. In some embodiments, changing the sweeping of the cryospray applicator includes: determining a position proximate to a no-go zone, determining a control signal directing infringing of the no-go zone, and controlling the sweeping of the cryospray applicator to avoid the no-go zone.

One aspect of the present disclosure relates to a skin cooling treatment system. The system includes a mechanical arm having a proximal end and a distal end, a cryospray applicator coupled to the distal end of the mechanical arm, and a processor. In some embodiments, the cryospray applicator includes an array of orifices. The cryospray applicator can be moveable by the mechanical arm to deliver a spray of cryogen to a portion of an area of skin tissue for treatment. In some embodiments, the processor can receive imagery of a portion of skin of a patient for receiving a skin cooling treatment and automatically identify boundaries from the received imagery to designate portions of the skin of the patient for receiving the skin cooling treatment. The processor can determine an instantaneous treatment footprint and generate a treatment path for the portion of skin of the patient designated for receiving the skin cooling treatment based on the treatment footprint. The processor can control the cryospray applicator to deliver the skin cooling treatment to the skin according to the treatment path.

In some embodiments, receiving imagery of the portion of skin of the patient includes generating imagery of the portion of the skin of the patient with a vision system coupled to the cryospray applicator. In some embodiments, the vision system is coupled to the distal end of the mechanical arm. In some embodiments, the imagery includes visible spectrum imagery and infrared imagery. In some embodiments, the processor can determine perfusion of the portion of skin designated for receiving the skin cooling treatment.

In some embodiments, the processor can adjust a dosing according to the perfusion of the portion of skin designated for receiving the skin cooling treatment. In some embodiments, delivering the skin cooling treatment includes advancing the cryospray applicator across the skin of the patient according to the treatment path. In some embodiments, the processor can receive temperature information from the treatment footprint and change the advancing of the cryospray applicator across the skin according to the temperature information. In some embodiments, the temperature information can include data characterizing an advance of freezing-front.

In some embodiments, automatically identifying boundaries can include: identifying a no-go feature, creating a no-go zone including the no-go feature and a safety offset at least partially surrounding the no-go feature, and creating boundary delineating between the no-go-zone and the portions of skin designated for receiving skin cooling treatment. In some embodiments, the treatment path prevents treatment in the no-go zone. In some embodiments, the processor can ascertain an attribute of the skin designated for receiving the skin cooling treatment before delivering the skin cooling treatment. In some embodiments, the attribute can be at least one of: a deformation; or a cooling response.

In some embodiments, determining the attribute of the skin includes: directing a spray at at least some of the skin designated for receiving the skin cooling treatment, and measuring a deformation of the at least some of the skin resulting from the directed spray. In some embodiments, the processor can modify the delivering of the skin cooling treatment based on the measured deformation of the at least some of the skin resulting from the directed spray. In some embodiments, the processor can select a nozzle. In some embodiments, the instantaneous treatment footprint is determined based on the selected nozzle.

In some embodiments, the processor can determine an attribute of the treated skin subsequent to the delivering of the skin cooling treatment. In some embodiments, the attribute can be at least one of: an erythema level or a re-warming rate. In some embodiments, the processor can deliver a rewarming treatment based on the determined attribute of the treated skin. In some embodiments, the processor can update a patient profile of the patient with information for adjusting a future treatment based on the determined attribute of the treated skin. In some embodiments, the processor can detect a motion of the patient, generate a modified treatment path based on the motion of the patient, and deliver the skin cooling treatment according to the modified treatment path.

DETAILED DESCRIPTION OF THE INVENTION

Figure 1:
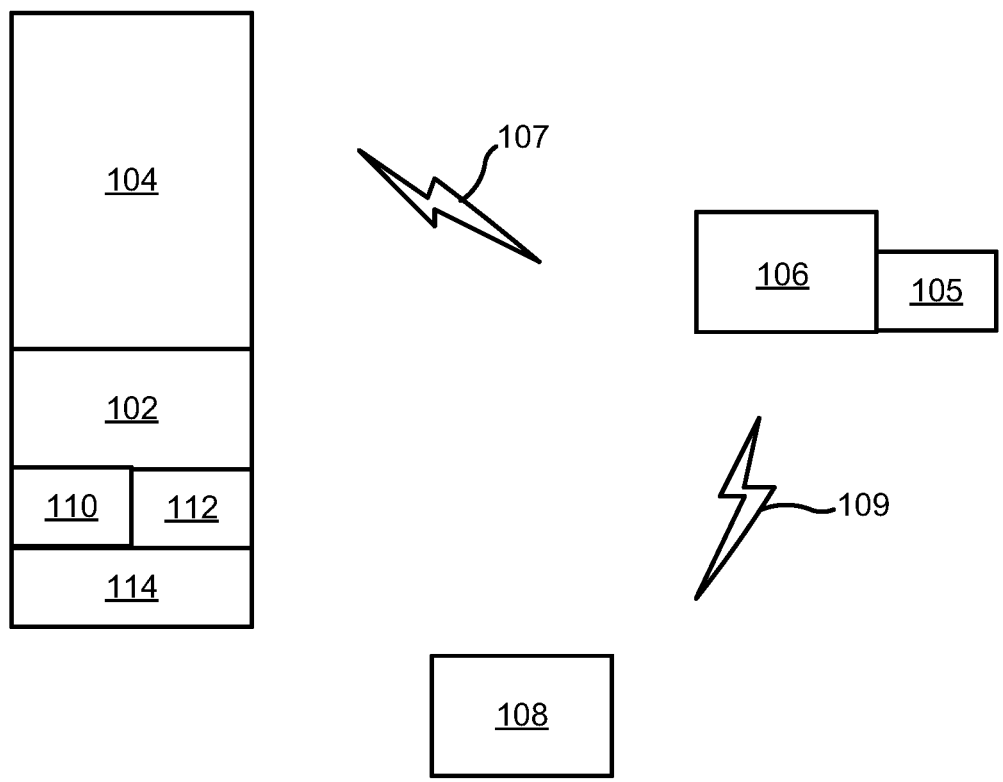
FIG. 1 is a schematic illustration of one embodiment of a skin cooling treatment system.

Cooling based treatments are frequently used to address a wide range of health and aesthetic issues. Some of these treatments have been specifically designed to create skin lightening. This skin lightening may be localized to a small skin area, or may affect a large area of skin. The area of to be treated skin can make such treatment difficult as adequate consistency of treatment may be difficult to achieve. These treatments can include cooling treated skin to specific temperatures and/or temperature ranges, and in some instances can include maintaining those temperatures and/or temperature ranges for a predetermined time and/or range of times. In some instances, the effectiveness of many treatments is dependent on the providing of specific amounts of cooling for specific amounts of time. Further, the difficulty in achieving consistent results increases as the treated area increases.

The present disclosure relates to systems, devices, and methods that improve the planning and/or delivery of a treatment. This improved planning and/or delivery of the treatment can be achieved by a system and/or by use of a system that includes a cryospray applicator coupled to a distal end of a mechanical arm that can be a multi-axis arm. The position and/or orientation of the cryospray applicator can be controlled by movement of the mechanical arm and/or by movement of one or several joints of the mechanical arm. The mechanical arm can be controlled to sweep the cryospray applicator across the patient's skin to treat a desired area of skin. The sweeping of the cryospray applicator can be controlled according to information received from one or several of the sensors including, for example, the temperature of the skin, the distance between the cryospray applicator and the skin being treated, and/or the orientation of the cryospray applicator with respect to the skin.

The cryospray applicator can include one or several sensors that can detect, for example, a distance between the cryospray applicator and the skin being treated, the orientation of the cryospray applicator with respect to the skin being treated, and/or the cooling or temperature of the skin being treated. The cryospray applicator can include a visualization system that can generate images of the patient and/or of portions of the patient before and/or during a treatment. In some embodiments, the visualization system can include a camera and/or an infrared camera. The cryospray applicator can further include a nozzle control, which nozzle control can change nozzles of the cryospray applicator to affect a size of treatment footprint of the cryospray applicator to provide a desired size of the treatment footprint. Nozzles can be changed to change the size of the treatment footprint to facilitate treatments of small skin areas and/or to provide improved dosing control.

The system can include a controller which can control the operation of the mechanical arm, the cryospray applicator, the sensors, the visualization system, and/or the nozzle control. The controller can receive information relating to the patient and the area of the patient's skin to be treated and can generate a treatment plan for the patient. The generation of the treatment plan can include the generation of one or several treatment paths, the identification of patient features, the ascertaining of one or several attributes of the patient's skin, or the like. The controller can direct operation of all or portions of the system to ascertain one or several attributes of the patient and/or of the patient's skin. This can include generating images of the patient and/or of the area of the patient's skin to be treated, ascertaining underlying skin structure of all or portions of the area of the patient's skin to be treated, and/or measuring perfusion of the skin and or the thermal response of the skin to cooling. The treatment plan can be used to control and/or direct the delivery of treatment to the patient. In some embodiments, the treatment plan may remain constant, and in some embodiments, the treatment plan can be modified as the treatment is being delivered.

With reference now to FIG. 1, a schematic illustration of one embodiment of a skin cooling treatment system 100 is shown. The skin cooling treatment system 100 can include a cryospray applicator 102 that is coupled to a mechanical arm 104, and specifically to a distal end of the mechanical arm 104. The cryospray applicator 102 can be configured to deliver a coolant to a treated portion of skin. In some embodiments, the cryospray applicator 102 can be configured to deliver a spray of cryogen towards and/or or onto a portion of skin being treated. This spray of cryogen can be delivered through one or several orifices, which orifices can comprise one or several nozzles. Embodiments of an exemplary cryospray applicator 102 including an array of orifices are disclosed in U.S. application Ser. No. 16/020,852, filed on Jun. 27, 2018, and entitled, "Dermatological Cryospray Devices Having Linear Array Of Nozzles And Methods Of Use", the entirety of which is hereby incorporated by reference herein. Further details of the mechanical arm 104 and the cryospray applicator 102 can be found in U.S. Provisional Application No. 62/784,052, filed on Dec. 21, 2018, and entitled "AUTOMATED CONTROL AND POSITIONING SYSTEMS FOR DERMATOLOGICAL CRYOSPRAY DEVICES," the entirety of which is hereby incorporated by reference herein.

The mechanical arm 104 can have any desired number of axes of movement, and can, in some embodiments, be a 6-axis arm. In some embodiments, the mechanical arm 104 can have a single degree of freedom (e.g. a linear stage) which would allow control of movement along one axis, two degrees of freedom which would allow control of movement along two axes, three degrees of freedom, four degrees of freedom, five degrees of freedom, six degrees of freedom, and/or any other number of degrees of freedom. In some embodiments, the number of degrees of freedom can be selected based on the desired level of control and movement of the cryospray applicator. Thus, a higher number of degrees of freedom provide greater control of the position and/or orientation of the cryospray applicator 102. The mechanical arm 104 can be any of a number of currently commercially available mechanical arms. The mechanical arm 104 can be robotic and/or teleoperated.

The system 100 can include a controller 106 and/or processor 106 which can be communicatively coupled with the mechanical arm 104 and specifically with one or several actuators in the mechanical arm 104. In some embodiments, the communicating coupling of the controller 106 and the mechanical arm 104 can be via a wired or wireless connection, and the communicating coupling is indicated by lightning bolt 107. The processor 106 can comprise a microprocessor, such as a microprocessor from Intel® or Advanced Micro Devices, Inc.®, or Texas Instrument, or Atmel, or the like.

The controller and/or processor 106 can be communicatingly coupled with a memory, which memory can be volatile and/or non-volatile and/or can include volatile and/or non-volatile portions. In some embodiments, the memory can include information relating to one or several patients, one or several planned treatments, and/or one or several delivered treatment. The memory relating to one or several patients can include, for example, a unique patient profile associated with each patient, and/or a unique provider profile associated with each provider. In some embodiments, a patient's patient profile can include information identifying one or several attributes of the patient including, for example, the patient's medical history, the patient's treatment history including, for example, information relating to one or several treatments provided to the patient, and/or information relating to the efficacy of one or several previously provided treatments. In some embodiments, the provider profile can include information relating to treatments provided to the provider's patients and/or the effectiveness of these provided treatments.

The memory 105 can include the information relating to one or several planned treatments. This information can include, for example, all or portions of information used in delivering a treatment. This can include, for example, information relating to one or several treatment paths, height and/or orientation specifications, dosing information, or the like. The memory 105 can further include a database with information relating to treatment results. This information can, for example, identify treatment effectiveness, information relating to one or several responses associated with a treatment, or the like. In some embodiments, this information can be specific to one or several patients and can be linked with the one or several patient profiles of those one or several patients.

The controller 106 and/or processor 106 can generate a treatment plan and can generate control signals which can control the movement of the cryospray applicator 102 according to the treatment plan. In some embodiments, the treatment plan can remain constant during the treatment, and in some embodiments, the treatment plan can be adjust as the treatment is being provided. The control of the movement of the cryospray applicator 102 can allow the processor 106 to control: the sweeping of the cryospray applicator 102 across the patient's skin; the distance between the cryospray applicator 102 and the portion of skin being presently treated; and/or the orientation of the cryospray applicator 102 with respect to the portion of skin being presently treated.

The controller 106 can, in some embodiments, receive information relating to the desired area of skin for treatment and information relating to the treatment. With this information, the controller 106 can, in some embodiments, generate treatment paths, which treatment paths characterize the movement of the cryospray applicator 102 and the delivery of cooling the cryospray applicator 102. In some embodiments, the controller 106 can change these treatment paths during the providing of a treatment. In some embodiments, for example, the size of the portion of skin treated at any instant by the cryospray applicator 102 may vary based on, for example, the nozzle being used to deliver the treatment, the number of orifices in the array of orifices through which cryogen is sprayed, the distance between the portion of skin being treated and the cryospray applicator 102, or the like. In such embodiments, as the size of the portion of skin treated at any instant changes, the controller 106 can generate updated treatment paths to compensate for this change in the size of the portion of skin treated at any instant.

The controller 106 can be communicatingly connected with a user device 108. The user device can be distinct from the controller 106, or in some embodiments, the user device 108 can include the controller 106. The user device 108 can be any device configured to provide information to and receive inputs from a user, such as the user controlling the treatment provided by the skin cooling treatment system 100. The user device 108 can, in some embodiments, comprise a computing device such as a laptop, a tablet, a smartphone, a monitor, a display, a keyboard, a keypad, a mouse, or the like. In some embodiments, the communicating coupling of the controller 106 and the user device 108 can be via a wired or wireless connection, and the communicating coupling is indicated by lightning bolt 109.

The cryospray applicator can include a sensing subsystem 110, a visualization subsystem 112, and/or a nozzle control 114. The sensing subsystem 110 can include a plurality of sensors 206. These sensors can include a plurality of sensors that can be configured to detect and/or determine a distance between the cryospray applicator 102 and/or an orientation of the cryospray applicator 102 with respect to the patient's skin, and specifically with respect to an instantaneous treatment footprint. The visualization subsystem 112 can comprise one or several cameras. These one or several cameras can comprise one or several cameras configured to generate image data, also referred to herein as imagery. The generated image data can include image data in the visible spectrum and/or image data in the non-visible spectrum. As used herein, "image data" can be any type of data generated by one or several cameras such as in the visualization system 112, this data including, for example, 2-D image data and/or 3-D image data. In some embodiments, the 2-D and/or 3-D image data can be still or video data. In some embodiments, the 3-D image data can include point-cloud data. The nozzle control 114 can identify a current nozzle used by the cryospray applicator, can identify a desired treatment footprint, and can select a next nozzle that best achieves the desired treatment footprint.

Figure 2:
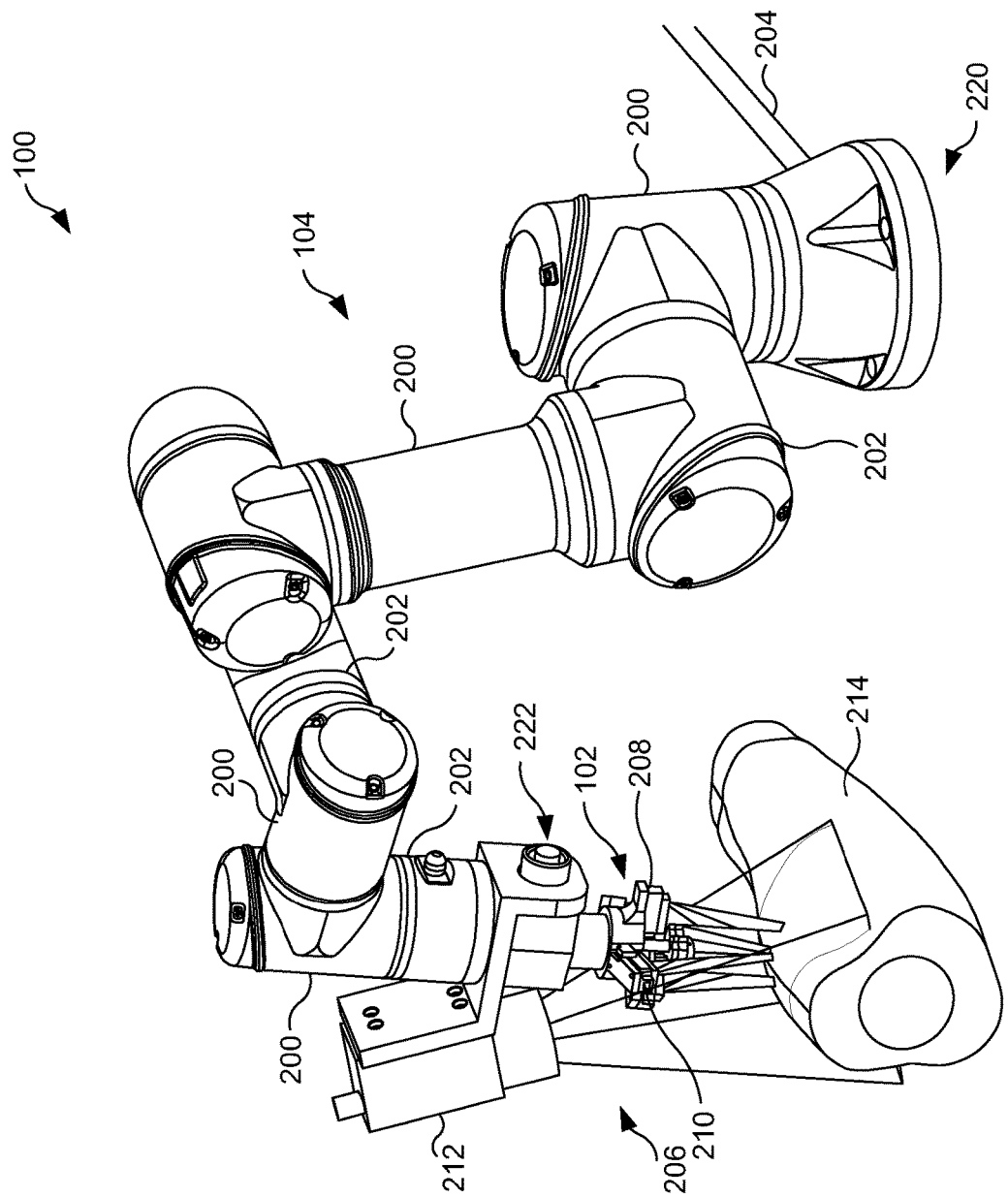
FIG. 2 is a perspective view of one embodiment of the skin cooling treatment system.

With reference now to FIG. 2, a perspective view of one embodiment of the skin cooling treatment system 100 is shown. The system includes the cryospray applicator 102 and the mechanical arm 104. As seen in FIG. 2, the mechanical arm 104 comprises a plurality of linkages 200 coupled by a plurality of joints 202, which joints 202 allow the relative movement of the linkages 200 with respect to each other. The mechanical arm 104 can further include a plurality of actuators, which actuators can, in response to control signals received from the controller 106, affect the relative position of some or all of the linkages 200 via movements of some or all of the joints 202 coupling linkages 200 to thereby affect the position and/or orientation of the cryospray applicator 102.

The mechanical arm 104 can further include one or several communication features such as cable 204. In some embodiments, the communication features, such as the cable 204 can communicatively couple the mechanical arm 104, and specifically the actuators of the mechanical arm 104, to the controller 106.

The mechanical arm 104 further comprises a proximal end 220 and a distal end 222. In some embodiments, the proximal end 220 of the mechanical arm 104 can be secured to an object such as, for example, a floor, a table, a cart, a wagon, or the like. The distal end 222 of the mechanical arm 104 can be coupled to the cryospray applicator 102 and can move with respect to the proximal end 220 of the mechanical arm 104. In some embodiments, the processor 106 can be configured to control the distal end 222 of the mechanical arm 104 and/or to control the cryospray applicator 102.

The cryospray applicator 102 can include a plurality of sensors 206, which sensors can include one or several alignment sensors 208, one or several distance sensors 210, and/or one or several temperature detection features 212. In some embodiments, the sensors 208, 210, 212 belong to the sensing subsystem 110. These sensors 206 can, in some embodiments, sense information relating to the treatment of a patient 214, and specifically to the treatment of some or all of the patient's skin.

Figure 3:
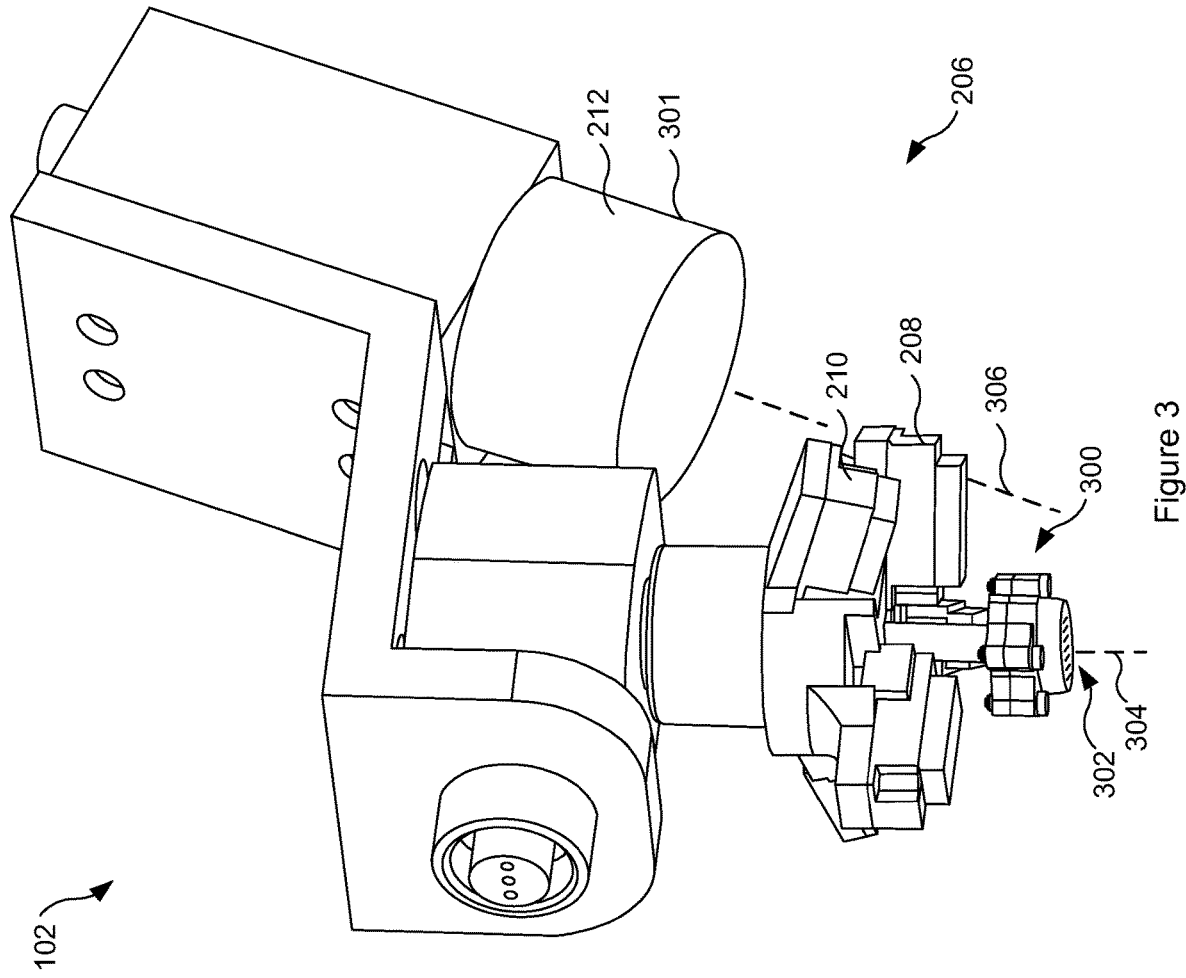
FIG. 3 is a perspective view of one embodiment of the cryospray applicator.

With reference now to FIG. 3, a perspective view of one embodiment of the cryospray applicator 102 is shown, which cryospray applicator 102 can be coupled to the distal end 222 of the mechanical arm 104. The cryospray applicator 102 includes a spray head 300 which comprises an array of orifices 302 through which cryogen can be sprayed towards and/or onto the patient's skin and specifically towards and/or onto a portion of the patient's skin being presently treated.

In some embodiments, the cryospray applicator 102 comprises the plurality of sensors 206, and specifically comprises one or more of: one or several alignment sensors 208; one or several distance sensors 210; or one or several temperature detection features 212. In some embodiments, the one or several temperature detection features 212 can be configured to: detect freezing of the portion of the patient's skin being presently treated; detect a temperature of the portion of the patient's skin being presently treated; detect a freezing rate of the portion of the patient's skin being presently treated, or the like. In some embodiments, the temperature detection feature can comprise a camera, and specifically can comprise an infrared camera 301. In some embodiments, the infrared camera 301 can be pointed at the portion of the patient's skin being presently treated, or in other words, an axis 304, also referred to herein as "the line of spray 304", centrally extending through the array of orifices 302 intersects with an axis 306 central to the field of view of the infrared camera 301 such that the portion of skin being presently treated is within the field of view of the infrared camera 301. In embodiments in which the one or several temperature detection features 212 comprises one or several cameras, the one or several temperature detection features 212 can belong to the visualization subsystem 112.

Figure 4:
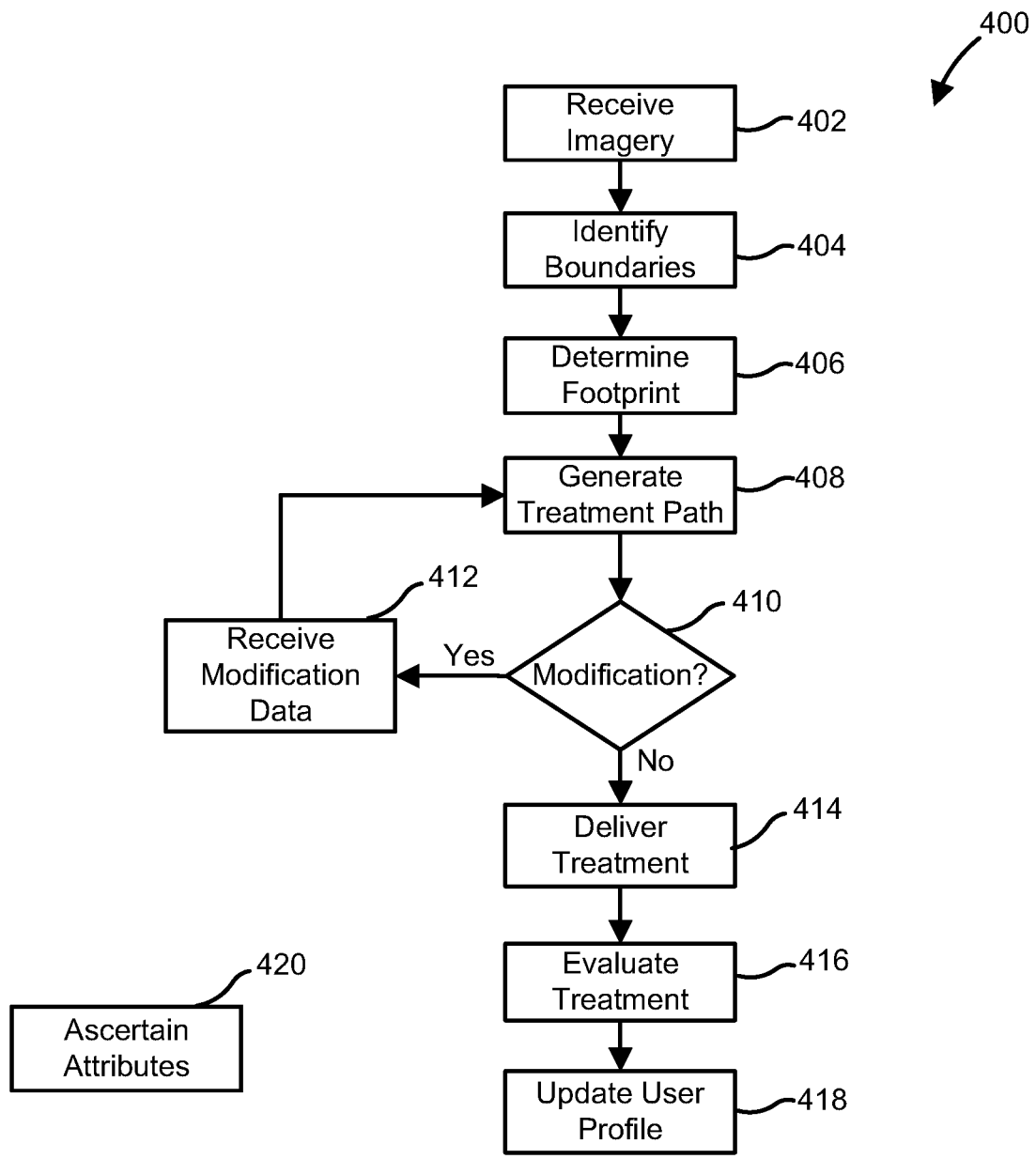
FIG. 4 is a flowchart illustrating one embodiment of a process for providing a skin cooling treatment.

With reference now to FIG. 4, a flowchart illustrating one embodiment of a process 400 for controlling a skin cooling treatment system 100 is shown. In some embodiments, the cooling system 100 can include a mechanical arm 104 that has a cryospray applicator 102 coupled to the distal end of the mechanical arm 104. The process 400 includes steps relating to the planning of the treatment, as well as to the delivery of the treatment. The process 400 can be performed by all or portions of the system 100 including by, for example, the processor 106.

Figure 5:
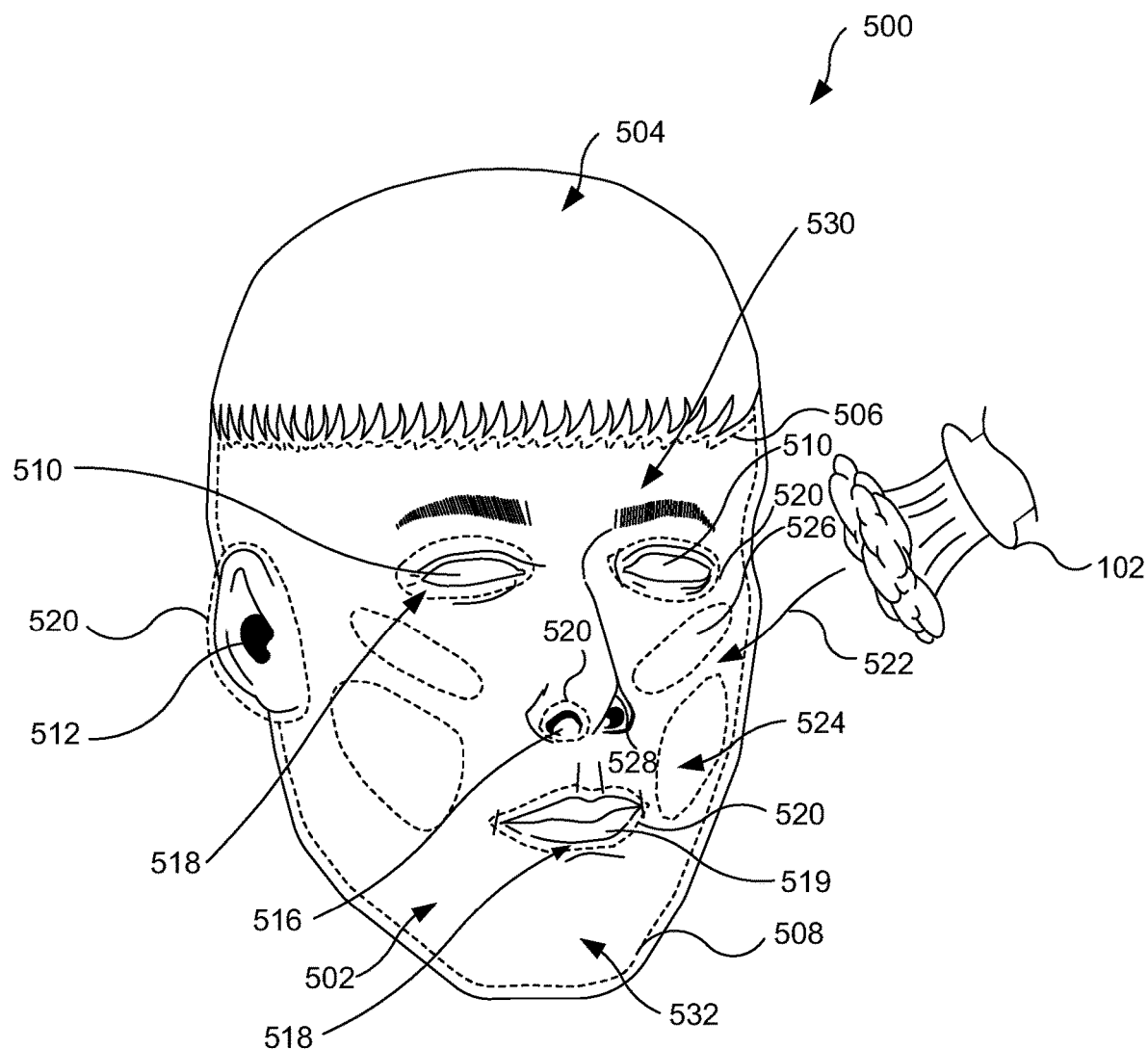
FIG. 5 is a schematic depiction of one embodiment of a patient's head.

With reference now to FIG. 5, an illustration of one embodiment of the patient's head 500 is shown. The patient's head 500 includes an area of skin designated for treatment 502, which area of skin designated for treatment is the patient's face, and an area of skin that is not designated for treatment 504, which area of skin not designated for treatment is covered by the patient's hair.

Returning again to FIG. 4, the process 400 begins at block 402, wherein imagery is received. In some embodiments, the imagery can be received from the visualization subsystem 112 and/or the visualization subsystem 112 can generate the images. In some embodiments, the images can be generated by one or several cameras that can be a part of the visualization subsystem 112. With reference to FIG. 5, in some embodiments, imagery can be generated of the area 502 of the patient's skin designated for treatment.

At block 404, one or several boundaries are identified of an area of skin designated for receiving treatment. In some embodiments, for example, an area of the patient's skin can be designated for receiving a treatment. This area of the patient's skin can be represented in imagery received in block 402. In some embodiments, the processor 106 can identify boundaries of the area of skin designated for treatment and can use the boundaries to limit the planning of the treatment as well as to limit delivery of treatment. In some embodiments, these boundaries can be identified based on one or several identifying features such as, for example, one or several anatomical landmarks. These anatomical landmarks can include, for example, one or several patient features that are sufficiently distinct to allow accurate identification in image data. In some embodiments, these landmarks can include, for example, a natural part of the patient such as all or parts of: a limb; a joint; a bone; a joint; a nipple; a nose, an eye, a mouth, a mole, a scar, or the like, and/or can include a created feature such as, all or parts of a tattoo, a piercing, or the like. In some embodiments, these boundaries can be identified based on a relative position with respect to these anatomical landmarks. The boundaries can be stored in the memory 105.

Referring to FIG. 5, the first boundary 506 delineates between the area 502 designated for treatment and the area 504 designated for no treatment. More specifically, the first boundary 506 delineates between the patient's face in the portion of the patient's head 500 covered by hair. A second boundary 508 identifies the outer limits of the patient's face and does the outer limits of the area 502 of the patient's skin designated for treatment. In some embodiments, the boundaries 506, 508 can be generated by the identification of anatomical landmarks in imagery generated of the patient's head 500, and specifically by identifying the portion of the patient's head 500 covered by hair and the outer limits of the patient's head 500.

Referring again to FIG. 4, at block 406 of the process 400 a treatment footprint is identified. The treatment footprint can identify a patch of skin being treated by the cryospray applicator 102 when delivering a spray of cryogen towards the patient at a specific location. In some embodiments, the treatment footprint, and specifically besides the treatment footprint can vary based on the nozzle used for delivering the cryogen spray, the distance separating the patches skin being treated and the cryospray applicator 102, the number and/or arrangement of orifices in the nozzle, and/or the alignment of the cryospray applicator 102 with respect to the patch of skin being treated by the cryospray applicator 102. In some embodiments, the treatment footprint can be selected based on one or several attributes of the area 502 of skin designated for treatment and/or based on one or several attributes of portions of that area 500 to a skin designated for treatment. In some embodiments, for example, large, flat portions of skin may be easily treated with a large treatment footprint, whereas more heavily contoured portions of skin may be better treated with a small treatment footprint. In some embodiments, the treatment footprint can be controlled by changing the distance between the cryospray applicator 102 and the patch of skin being treated, by changing the alignment of the cryospray applicator 102. With respect to the patch of skin being treated, and/or by changing the nozzle of the cryospray applicator 102. In some embodiments, the nozzle can be changed and/or selected by the nozzle control 114. In some embodiments, the nozzle control 114 can be controlled by the processor 106. The treatment footprint can be determined by the processor 106.

Figure 6:
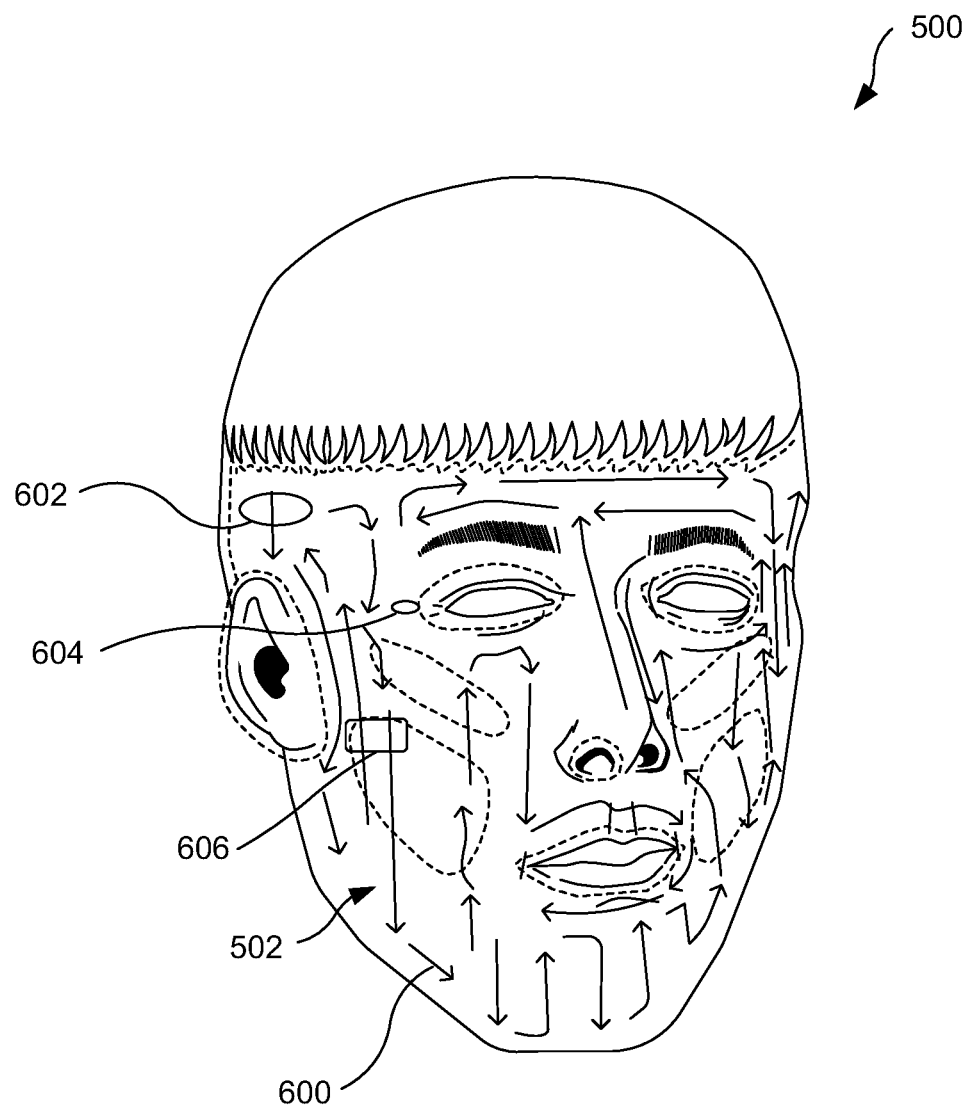
FIG. 6 is a schematic depiction of one embodiment of a patient's head including treatment paths.

With reference now to FIG. 6, a schematic illustration of the patient's head 500 is shown. The patient's head 500, and specifically the area 502 of the patient's skin designated for treatment shows overlaying treatment paths 600 in the form of a plurality of arrows. Also shown in FIG. 6 are outlines of three potential treatment footprints 602, 604, 606. Each of these footprints 602, 604, 606 comprises a different size, and a different shape with footprint 606 being rectangular, and the largest of the footprints 602, 604, 606, and footprint 604 being oval-shaped and the smallest of the footprints 602, 604, 606. As soon, footprint 606 is being used to treat portions of the patient's skin corresponding to cheeks and footprints 604 is being used to treat around the patients eye. These footprints can be selected by the processor 106 to provide a desired treatment and/or a desired level of control of the treatment.

At block 408, a treatment path is generated. The treatment path can control the movement of the cryospray applicator 102 with respect to the area 502 of the patient's skin being treated. In some embodiments, the treatment path can specify, for example, a dosing for the treatment, a sweeping speed defining the speed with which the cryospray applicator 102 moves across the patient's skin, the height at which the cryospray applicator 102 is positioned above the patch of skin being treated, the alignment of the cryospray applicator 102 with respect to the patch of skin being treated, and/or the sweeping movement of the cryospray applicator 102 across the patient's skin. The treatment path can be generated by the processor 106 based on, for example, the imagery received in block 402, one or several of the boundaries identified in block 404, and/or the footprint determined in block 406.

After the treatment path has been generated, the process 400 proceeds to decision state 410, wherein it is determined if a modification of the generated treatment path has been specified, and/or provided. In some embodiments, for example, a medical provider may receive information related to the generated treatment path, and may opt to change one or several attributes of that treatment path. In some embodiments, the medical provider may provide information to the system 100, indicating modifications to the treatment path. If it is determined that a modification to the generated treatment path has been requested, than the process 400 can proceed to block 412, wherein modification data can be received from the medical provider, and the process 400 can then return to block 408 and generate the treatment path as described above, but including the received modification data.

Returning again to decision state 410, if it is determined that no modification has been requested, than the process 400 proceeds to block 414, wherein the treatment is delivered. In some embodiments, the treatment can be delivered according to the generated treatment path, and specifically, the treatment can be delivered by cooling all or portions of the skin in the area 502 designated for treatment. In some embodiments, the providing of the treatment can include the directing of the cryogen spray towards skin in the area 502 designated for treatment, and specifically towards patches of skin within the area 502 of skin designated for treatment. In some embodiments, while the cryogen is being sprayed, the cryospray applicator 102 can be swept across the area 502 of the patient's skin designated for treatment. The sweeping of the cryospray applicator 102 across the area 502 of the patient's skin designated for treatment, the height and/or the alignment of the cryospray applicator 102 with respect to the patch of skin being treated, and/or dosing can be modified during the treatment based on information relating to the patient and gathered during the treatment. This information can include, for example, information relating to: skin deformation; skin temperature; skin cooling; skin rewarming; erythema; perfusion; and/or patient movement. In some embodiments, the treatment can be delivered by the cryospray applicator 102 according to one or several control signals generated by the processor 106.

After the treatment has been delivered and/or simultaneous with the delivery of treatment, the process 400 proceeds to block 416, and evaluates the treatment. In some embodiments, this can include gathering of information relating to treated skin. This information can include, for example, data characterizing rewarming of the skin, data characterizing post-treatment temperature of the skin, data characterizing erythema of treated skin, or the like. This information can be gathered by the sensing subsystem of 110 and/or by the visualization subsystem 112. This gathered information can be analyzed by the processor 106 to characterize treatment effectiveness as substandard, meeting standards, or exceeding standards. In some embodiments, for example, rewarming data for the skin can be compared to one or several threshold values to determine whether the skin is rewarming too quickly, too slowly, or at the right speed. Similarly, erythema data can be compared to one or several threshold values to determine whether the erythema is insufficient, sufficient, or excessive. In some embodiments, if it is determined that the skin is rewarming too slowly, a warming treatment can be applied to the skin to increase the rewarming rate. Alternatively, if it is determined that the skin is rewarming too quickly, a cooling treatment can be applied to the skin to decrease the rewarming rate.

After the evaluation of the treatment effectiveness, the process 400 proceeds to block 418, wherein memory 105 is updated based on the treatment evaluation. In some embodiments, this can include the update of the patient profile with information characterizing the treatment result and/or the effectiveness of the treatment. In some embodiments, for example, indicia of modifications to treatment parameters for any future treatments for one or several patients, and specifically for the patient who received the treatment in the process 400 of FIG. 4, can be stored in the memory 105. In some embodiments, for example, the indicia modification can specify, the incrementing and/or decrementing of one or several treatment parameters used for the treatment provided in the process 400 for any future treatments.

At block 420, one or several attributes of skin to be treated, skin being treated, and/or skin that has been treated is determined. These attributes can include, for example, perfusion, deformation, elasticity, rewarming, temperature, or the like. In some embodiments, the step of block 420 can be performed before delivering of the treatment in block 414, and more particularly can be performed before generating of the treatment path in block 408. In some embodiments, block 420 can be performed after or simultaneous with delivering the treatment in block 414. In some embodiments, these one or several attributes can be ascertained via a preliminary sweep across all or portions of the area 502 of the patient's skin designated for treatment. In some embodiment, and as part of this sweep, cryogen or other liquid and/or gas can be sprayed on the skin as the cryospray applicator 102 is swept across the patient's skin to determine a deformation of the patients skin and/or to characterize one or several structures underlying the patient's skin. These structures can include, for example, bone, muscle, adipose tissue, or the like. In some embodiments, image data can be generated as part of this sweep, either in connection with spray of cryogen or independent of a cryogen spray. In some embodiments, this image data can include infrared image data which can be used to determine perfusion, temperature, and/or rewarming of the skin included in the sweep.

Figure 7:
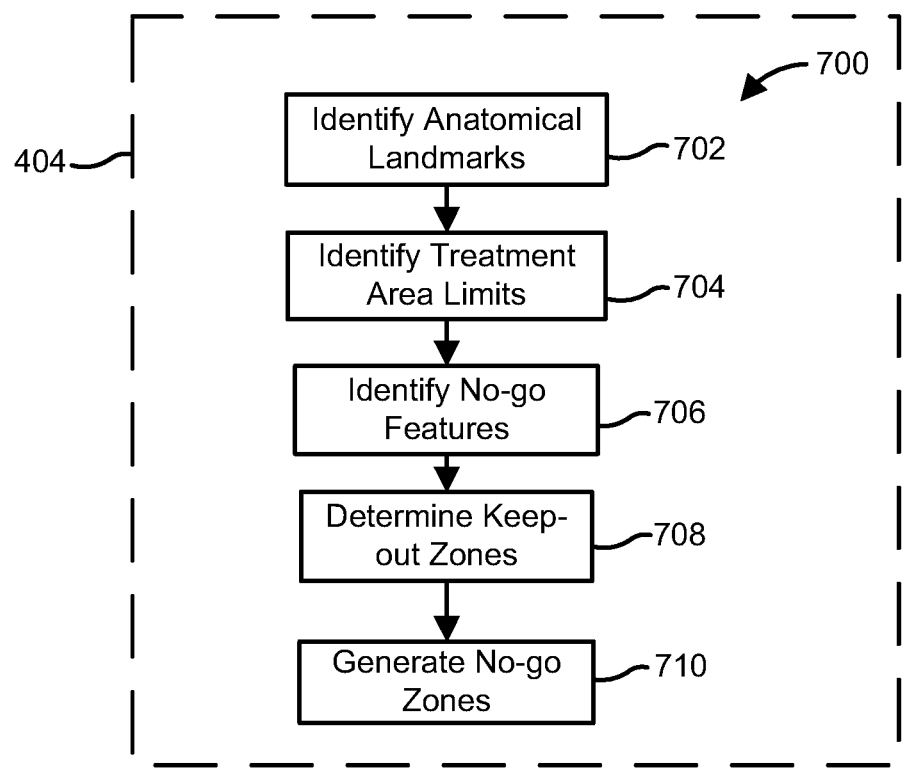
FIG. 7 is a flowchart illustrating one embodiment of a process for identifying boundaries.

With reference now to FIG. 7, flowchart illustrating one embodiment of a process 700 for identifying boundaries is shown. The process 700 can be performed as a part of, or in the place of the step of block 404 of FIG. 4. The process 700 begins a block 702 wherein one or several anatomical landmarks identified within the imagery received a block 402 of FIG. 4. At block 700 for, one or several treatment area limits are identified. In some embodiments, these treatment area limits correspond to the boundaries 506, 508 shown in FIG. 5

At block 706, one or several no-go features are identified. In some embodiments, a no-go feature is a feature that should not receive treatment and/or that's not receive any treatment. In some embodiments, no-go features include one or several sensitive portions of the body and/or portions of the body that could be damaged via treatment. In some embodiments, exemplary no-go features can include eyes, ears, lips, nostrils, any body orifice, or any other sensitive area or organ. As seen in FIG. 5, the patient's head 500 includes no-go features including eyes 510, ears 512, lips 514, and nostrils 516. The no-go features can be identified using the processor 106, and specifically via the use of the processor in connection with image recognition software, pattern recognition software, and/or artificial intelligence.

After the no-go features have been identified, the process 700 proceeds to block 708 wherein one or several keep-out zones are identified. In some embodiments, a keep-out zone (indicated as 518 in FIG. 5) identifies a buffer space around a no-go feature for which no treatment is received and would serve to protect the no-go feature. In some embodiments, a single buffer space, or in other words, a buffer space having a single width can be used for all no-go features, and in some embodiments, multiple buffer spaces may be used such that certain no-go features have larger buffer spaces, as compared to other no-go features. In some embodiments, for example, more sensitive no-go features may have larger keep-out zones as compared to less sensitive no-go features. The keep-out zones can be identified by the processor 106, with information from the memory 105 and based on the identified no-go features.

At block 710 one or several no-go zones are created. In some embodiments, a no-go zone is a combination of a no-go feature in the keep-out zone surrounding the no-go feature. In some embodiments, no-go zones can be generated by the generation of no-go boundaries (indicated as 520 in FIG. 5) around the no-go zones and the storing of the no-go boundaries in the memory. In some embodiments, and no-go zones identified in block 710 can be used in the generating of treatment paths.

Figure 8:
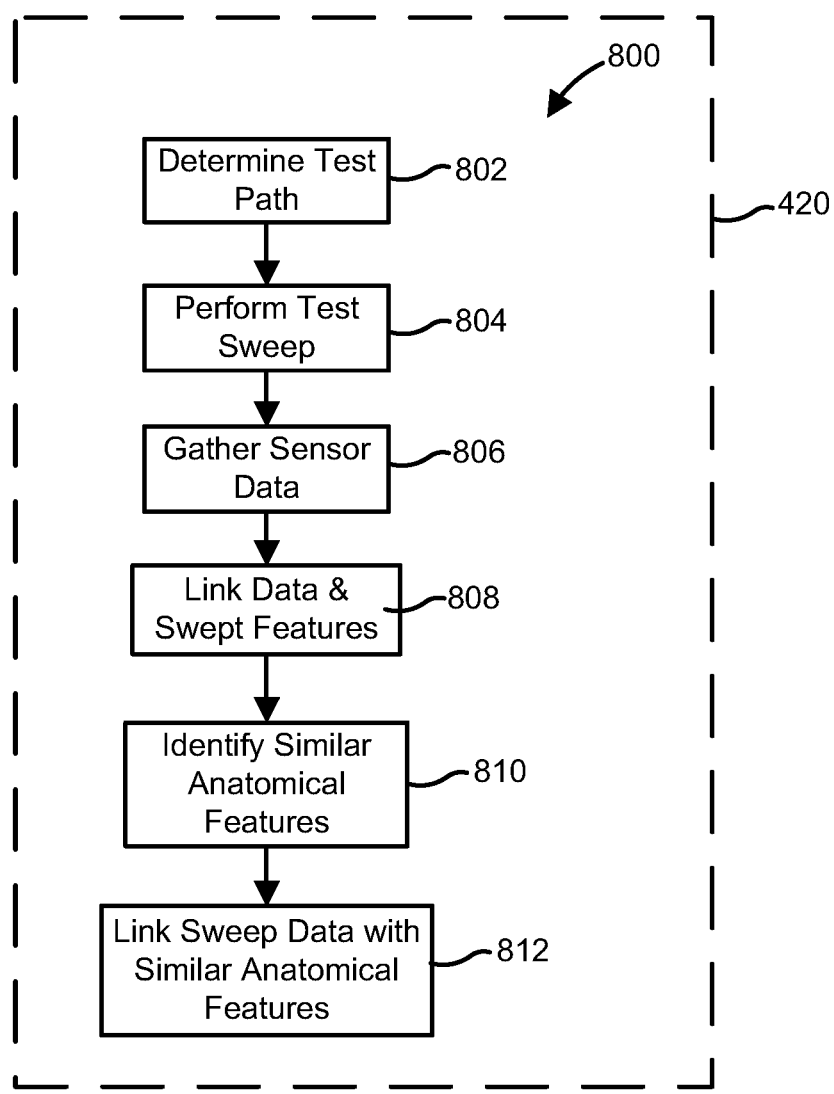
FIG. 8 is a flowchart illustrating one embodiment of a process for ascertaining attributes of skin designated for treatment.

With reference at a FIG. 8, flowchart illustrating one embodiment of a process 800 for ascertaining attributes of skin is shown. The process 800 can be performed as a part of, or in the place of the step of block 420 of FIG. 4. The process 800 begins a block 802 wherein a test path is determined. In some embodiments, the test path can be a path for sweeping the cryospray applicator 102 across some portion of the area 502 designated for treatment. In some embodiments, the test path (indicated by arrow 522 in FIG. 5) can be selected to sweep across some or all of the anatomical features within the area 502 of the patient's skin, which anatomical features can be identified from the image data received in block 402 via, for example, the processor 106 and specifically via the processor 106 executing image recognition software, pattern recognition software, and/or AI software. In some embodiments, the AI software can comprise an AI model that can be trained and loaded in the system 100. In some embodiments, the AI model can provide an output which is viewable by the provider. Any provider inputs can be gathered and can be used to update the training of the AI model. In some embodiments, for example, provider inputs can be gathered from multiple systems at a central server and can be used to update the training of the AI model. Updated training information can then be provided to at least the systems from which the provider inputs were gathered.

With reference to FIG. 5, this test sweep can include sweeping across, the hollows 524 of the cheeks, the cheeks 526, the nose 528, the forehead 530, and/or the chin 532. In some embodiments, the test sweep can cross these anatomical features as these anatomical features may have different attributes. For example, in some embodiments, the hollows 524 of the cheeks may be more deformable and/or so acceptable to greater deformation in the cheeks 526 and specifically then the portion of the cheeks directly above the cheekbones. The test path can be determined by the processor 106.

After the test path has been determined, the process 800 proceeds to block 804 wherein the test sweep is executed. In some embodiments, the test sweep can be executed by the controlled sweeping of the cryospray applicator across the patient's skin according to the test path. At block 806, sensor data and/or image is gathered during the test sweep. In some embodiments, the sensor data can be gathered by the sense subsystem 110 and the image data can be gathered by the visualization subsystem 112.

At block 808 the data gathered in step 806 can be linked with swept features. Specifically, one or several features crossed by the test sweep can be identified from the image data and can be linked to data gathered in step 806. In some embodiments, this can include linking deformation data, perfusion data, rewarming data, elasticity data, temperature data, and/or the like to features identified from the image data gathered during the test sweep. At block 810, features found throughout the area 502 and that are similar to the features identified in block 806 are identified, and in block 812, the data linked with swept features in block 808 is linked with features found throughout the area 502 and that are similar to the features identified in block 806.

Figure 9:
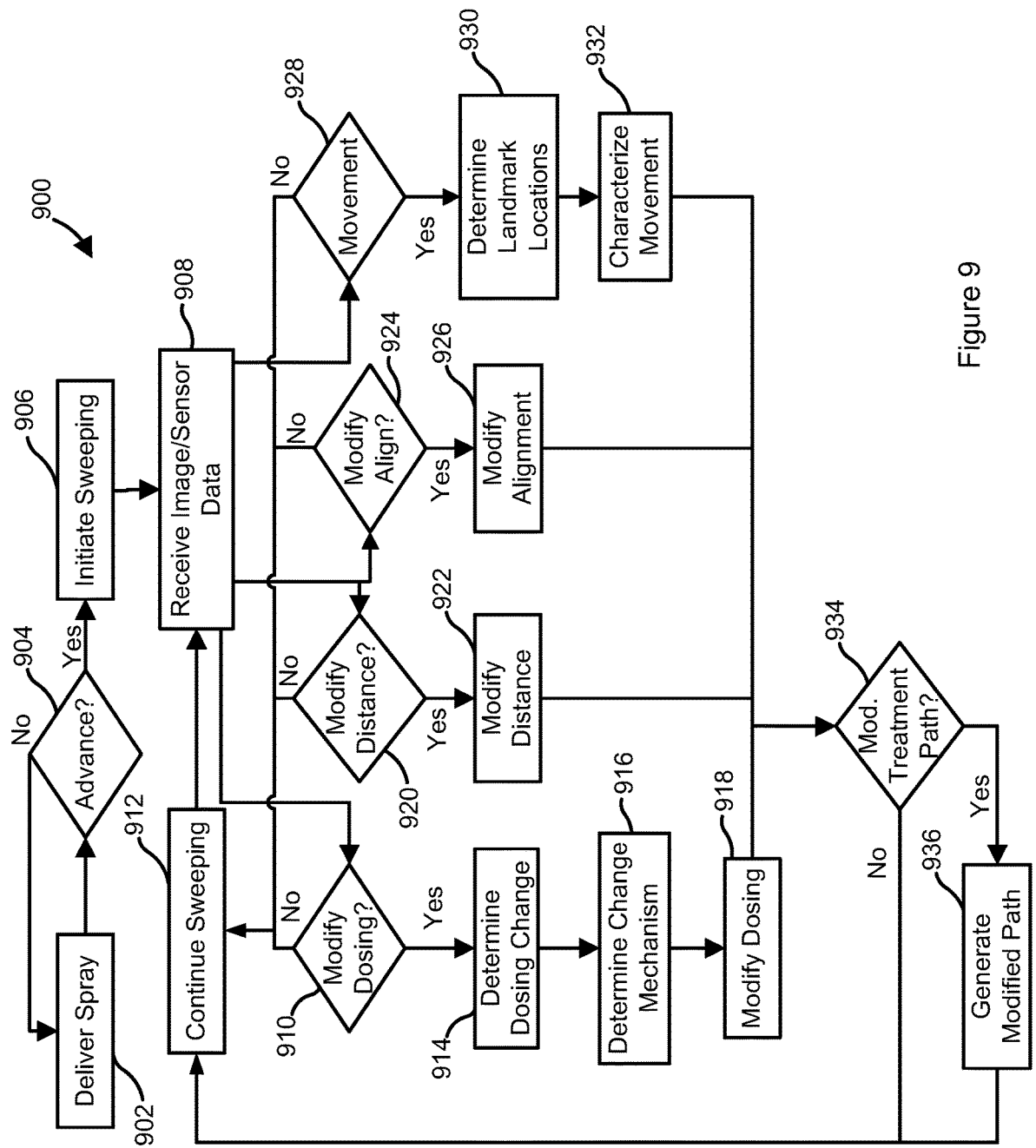
FIG. 9 is a flowchart illustrating one embodiment of a process for providing treatment.

With reference now to FIG. 9, a flowchart illustrating one embodiment of a process 900 for delivering a treatment is shown. The process 900 can be performed as a part of, or in the place of step 414 of FIG. 4. The process begins at block 902, wherein a spray of cryogen is delivered. In some embodiments, the spray of cryogen can be delivered by the cryospray applicator 102 and the spray of cryogen can be delivered towards the patients skin, and specifically towards a patch of skin within the area 502 designated to be treated. In some embodiments, the spray can start being delivered in block 902 and can continue to be delivered during some or all of the steps of process 900.

After the starting of the delivering of the spray, the process 900 proceeds to decision state 904, wherein it is determined whether to start to advance the cryospray applicator 102. In some embodiments, for example, the events of the cryospray applicator 102 can be delayed until one or several conditions and/or criteria are met for starting and/or for continuing to advance the current spray applicator 102. In some embodiments, for example, these criteria include, for example, temperature, the patch of skin being presently treated dropping below a threshold value, advancing of a freeze front beyond the patch of skin being presently treated at greater than a threshold speed, or the like. If it is determined that these criteria and/or conditions are not met, then the process 900 returns to block 902 and continues delivering the spray and waits until the conditions and/or criteria are met.

Returning again to decision state 904, if it is determined that the conditions and/or criteria are met, than the process 900 proceeds to block 906 wherein sweeping of the cryospray applicator across the area 502 of skin to be treated is initiated. In some embodiments, the sweeping can be initiated by the processor 106, which can generate control signals to control the operation of the cryospray applicator 102 and/or the mechanical arm 104.

At block 908 image and/or sensor data is received. In some embodiments, the image data can be received from the visualization subsystem 112 and the sensor data can be received from the sensing subsystem 110 some embodiments, and although a depiction is occurring after the initiating of the sweeping 906, the image and/or sensor data can begin been received simultaneous with and/or subsequent to delivering of the spray of block 902 and can continue throughout the performing the process 900. In some embodiments, the image, and/or sensor data can be received by the processor 106.

At decision state 910, it is determined whether to modify dose. In some embodiments, this determination can be made based on image, and/or sensor data received in block 908. In some embodiments, dosing can be modified based on measure temperature of the patch of skin being presently treated, based on a cooling rate of the patch of skin being presently treated, based on a rewarming rate of a patch of skin previously treated, or the like. If it is determined that no modification of dosing is needed and/or is desired, then the process 900 continues as depicted by the advance to block 912, wherein sweeping continues and by the advance to block 908, wherein image, and/or sensor data is received.

If it is determined that a dosing modification is needed, then the process 900 proceeds to block 914, wherein the dosing change is determined. In some embodiments, the determination of dosing change can comprise quantification of the desired change the dosing. This can include a determination of the desired increase and/or decrease in the dosing. In some embodiments, this change can be determined based on the image, and/or sensor data received in block 908. In some embodiments, for example, if it is determined that the temperature of the patch of skin being treated is too low, then the dosing can be decreased, alternatively, if it is determined that the temperature of the patch of skin is too high, then the dosing can be increased. The determination of the dosing change can be made, in some embodiments, by the processor 106.

After the dosing changes have been determined, the process proceeds to block 916, wherein the change mechanism is determined. In some embodiments, for example, dosing can be changed by a change to the treatment footprint, and specifically to the size of the treatment footprint.

In some embodiments, for example, the rate of cryogen sprayed by the nozzle of the cryospray applicator 102 can be constant and thus the increasing of the size of the treatment footprint can decrease the dosing and decreasing the size of the treatment footprint can increase the dosing. In some embodiments, the size of treatment footprint can be affected by changing a distance between the cryospray applicator 102 and the patch of skin being treated, and/or by changing the nozzle, and/or nozzle configuration including the number and/or arrangement of open orifices in the nozzle. In some embodiments, dosing can be changed by varying pressure of the cryogen in the nozzle, changing the sweeping speed of the nozzle across the skin being treated, and/or changing alignment of the nozzle with respect to the patch of skin being treated. In some embodiments, the change mechanism can be selected based on capabilities of the system 100 and/or based on one or several system preferences. In some embodiments, for example, the system 100 may include a preference for changing dosing via changing the distance separating the cryospray applicator 102 from the patch of skin being presently treated and/or by changing the sweeping speed up cryospray applicator 102. After the change mechanism for modifying the dosing has been determined, the process 900 proceeds to block 918, wherein the dosing is modified according to the determine dosing change of block 914 and according to the change mechanism determined in block 916.

At decision state 920, it is determined whether to change the distance separating the cryospray applicator 102 from the patches skin being presently treated. In some embodiments, this determination is independent of the determination as to whether to modify the dosing, and the determination may be based on information received from the sensing subsystem 110, and specifically based on information received from the distant sensors 210 in the sensing subsystem 110. If it is determined that no modification of distance is needed and/or is desired, then the process 900 continues as depicted by the advance to block 912, wherein sweeping continues and by the advance to block 908, wherein image, and/or sensor data is received.

If it is determined that modification to distance is needed, then the process 900 proceeds to block 922 wherein the distance separating the cryospray applicator 102 and the patch of skin being presently treated is modified. In some embodiments, this can include the generation, by the processor 106, of one or several control signals directing the mechanical arm 104 to move the cryospray applicator 102, either closer to or farther from the patches skin being presently treated. These one or several control signals can be provided by the processor 106 to the mechanical arm 104.

At decision state 924, it is determined whether to modify the alignment of the cryospray applicator 102 with respect to the patches of skin being presently treated. In some embodiments, this determination is independent of the determination as to whether to modify the dosing, and the determination may be based on information received from the sensing subsystem 110, and specifically based on information received from the orientation sensors 208 in the sensing subsystem 110. If it is determined that no modification of alignment is needed and/or is desired, then the process 900 continues as depicted by the advance to block 912, wherein sweeping continues. The process 900 then continues to advance to block 908, wherein image, and/or sensor data is received.

If it is determined that modification to the alignment is needed, then the process 900 proceeds to block 926 wherein the alignment is modified. In some embodiments, this can include the generation, by the processor 106, of one or several control signals directing the mechanical arm 104 to move the cryospray applicator 102 to change the alignment of the cryospray applicator 102 with respect to the patch of skin being presently treated. These one or several control signals can be provided by the processor 106 to the mechanical arm 104.

At decision state 928, it is determined whether the patient has moved, and specifically whether the patient has moved such that the area 502 of skin designated for treatment is in a different position and/or orientation with respect to the system. In some embodiments, this determination can be made using image data received in block 908, and specifically by comparing the location of one or several anatomical landmark locations in the present image data to the locations of those same anatomical landmarks in earlier generated image data. In some embodiments, if the location of one or several of the landmarks has changed by more than a threshold amount, then a movement can be determined. If it is determined that there has been no movement, then the process 900 continues as depicted by the advance to block 912, wherein sweeping continues and by the advance to block 908, wherein image, and/or sensor data is received.

If it is determined that there has been a movement, then the process 900 proceeds to block 930, wherein the locations of the anatomical landmarks are determined. In some embodiments, these locations can be determined by the processor 106 via, for example, image analysis, image recognition, and/or pattern recognition. In some embodiments, the processor 106 can determine the location of these one or several anatomical landmarks, and specifically can determine the pixels corresponding to each of some or all of the one or several anatomical landmarks.

After the landmark locations have been determined, then the process 900 proceeds to block 932, wherein the movement of the landmarks is characterized and/or is quantified. In some embodiments, this can include determining the distance moved by each of some or all of the anatomical landmarks. This determination can be made by comparing the current locations of each of some or all of the anatomical landmarks to previous locations of those same anatomical landmarks. A distance between the current and previous locations of each of the some or all of the anatomical landmarks can be determined. The characterization of the movement can be made by the processor 106.

After any of blocks 918, 922, 926, 932, the process 900 proceeds to decision state 934, wherein it is determined whether to modify the treatment path. In some embodiments, this determination can be made based on whether the change to any of the dosing, distance, and alignment, and/or the movement of the patient is sufficient to cause a change to the treatment path. In some embodiments, this determination can be made via comparison of any modifications and/or movements to one or several thresholds. In such an embodiment, a modification to the treatment path can be determined if the modification and/or movement is greater than and/or equal to the threshold. If it is determined that a modification to the treatment path is unnecessary, then the 900 continues as depicted by the advance to block 912, wherein sweeping continues and by the advance to block 908, wherein image, and/or sensor data is received.

If it is determined that a modification to the treatment path is needed, then the process 900 proceeds to block 936, wherein a modified treatment path is generated. In some embodiments, the modified treatment path can be generated in the same manner as the original treatment path was generated in block 408 of FIG. 4. However, the modified treatment path can be generated, in part based on inputs associated with the modifications of one or more of blocks 918, 922, 926 and/or the characterized movement of block 932. After the modified path has been generated, the process 900 proceeds to block 912, and continues sweeping. In some such embodiments, the continued sweeping is according to the modified treatment path.

Figure 10:
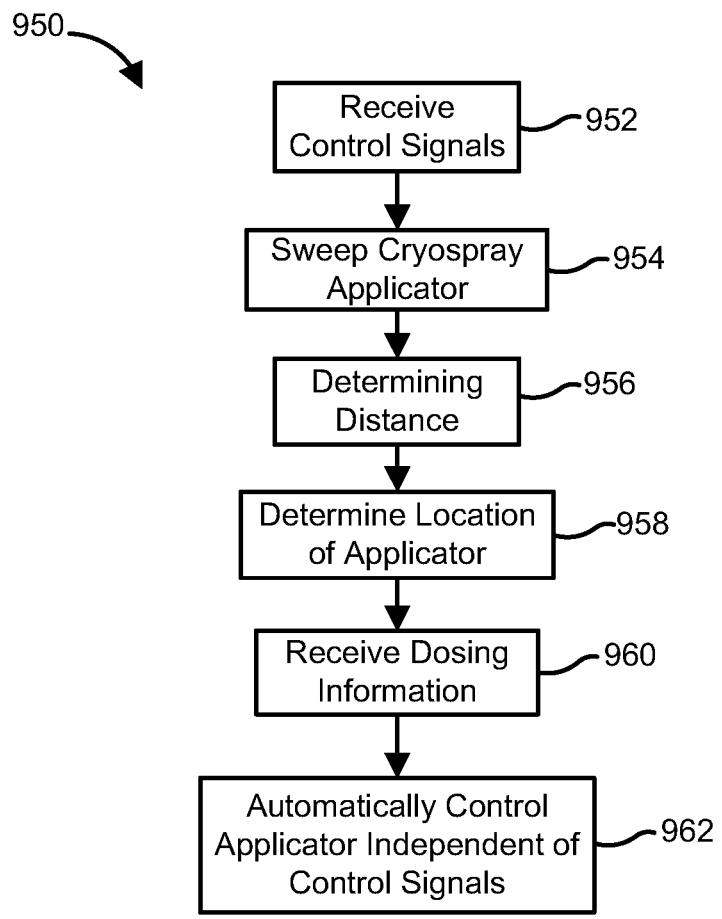
FIG. 10 is a flowchart illustrating one embodiment of a process for hybrid treatment control.

With reference now to FIG. 10, a flowchart illustrating one embodiment of a process 950 for hybrid treatment control is shown. In some embodiments, the mechanical arm 104 and/or the cryospray applicator 102 can be controlled according to control signals based on one or several provider inputs and according to control signals generated by the processor 106. In some embodiments, for example, a medical service provider can, via a user input device, provide inputs for controlling the movement of the cryospray applicator, and particularly for controlling the sweeping of the cryospray applicator 102. In some embodiments, some or all of these movements may, for example, provide improper dosing, lead to treating a no-go zone, or the like. In some embodiments, hybrid control provides freedom to the medical service provider to control the treatment, while at the same time simplifying the providing of the treatment and maintaining safety precautions.

The process 950 begins at block 952, wherein one or several control signals and/or user inputs are received from the medical service provider. In some embodiments, these control signals and/or user inputs can be received via a user input such, for example, a control stick, a control ball, a mouse, a keypad, a touch screen, a tracking pad, or the like. These control signals and/or user inputs can, in some embodiments, direct the sweeping of the cryospray applicator 102 across the skin in the area 502 designated for treatment. In some embodiments, the user inputs received in block 952 can be received by the processor 106, which can generate control signals to control the movement and/or sweeping of the cryospray applicator 102 according to the received user inputs. These control signals can control the movement of the cryospray applicator 102, and in some embodiments, as indicated at block 954, the cryospray applicator is swept across the skin in the area 502 according to the control signals and/or user inputs received in block 952.

During the sweeping of the cryospray applicator, data can be gathered from the sense subsystem 110 and/or the visualization subsystem 112. This information can be received by the processor 106, and based on this information, the distance between the cryospray applicator 102 and the patch of skin being presently treated can be determined as indicated in block 956 and/or the location of the cryospray applicator 102 can be determined as indicated in block 958. In some embodiments, the location of the cryospray applicator 102, or more specifically, the location of the patch of skin being presently treated with the area 502 of the patient's skin designated for treatment, can be determined based on data gathered by the visualization subsystem 112. In some embodiments, the relative position of one or several anatomical landmarks can be determined based on the data gathered by the visualization subsystem 112. The distance separating the cryospray applicator 102 and the patch of skin being presently treated and/or the location of the cryospray applicator 102 can be determined with the processor 106.

At block 960, dosing information is received. In some embodiments, this information can characterize the treatment dosage being delivered to the patch of skin being presently treated. This dosage can, in some embodiments, be characterized based on effects of the dosing such as, for example, the temperature of the patch of skin being presently treated, the rate of cooling of the patch of skin being presently treated, the advancing of the freezing-front, or the like. In some embodiments, the dosage can be characterized based on combined attributes of the position and/or movement of the cryospray applicator 102. In some embodiments, for example, the sweeping speed of the cryospray applicator 102, the size of the treatment footprint, and a rate of cryogen spraying can together characterize the dosage can together comprise the dosing information. The dosage information can be received by the processor 106.

At block 962, the applicator 102 is automatically controlled independent and/or partially independent of the control signals and/or user inputs received in block 952. In some embodiments, the cryospray applicator 102 can be moved independent and/or partially independently of the control signals and/or received user inputs based on at least one of: the distance between the patch of the skin being presently treated and the cryospray applicator; the location of the cryospray applicator 102, or the dosing information. The automatic moving of the cryospray applicator 102 independent of and/or partially independent of control signals and/or user inputs received in block 952 can include, for example, changing a sweeping speed of the cryospray applicator, changing the sweeping and/or sweeping motion of the cryospray applicator, or changing the distance between the portion of the skin of the patient and the cryospray applicator.

In some embodiments, the sweeping of the cryospray applicator 102 can be changed based on the position of the cryospray applicator and/or the treatment footprint being proximate to and/or sufficiently proximate to a no-go zone, and based on the determination of receipt of a user input and/or control signal in block 952 directing treatment of the no-go zone. In such an embodiment, the processor 106 may modify control signals generated based on the received user inputs to control sweeping of the cryospray applicator 102 to reflect the received user inputs while also avoiding the no-go zone.

In some embodiments, the cryospray applicator 102 can be further controlled to maintain a desired distance between the cryospray applicator 102 and the patch of skin being presently treated, and/or to maintain a desired dosing. In some embodiments, this can include control of the cryospray applicator 102 independent and/or partially independent of the user inputs received in block 952.

The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A skin cooling treatment system comprising:
a mechanical arm having a proximal end and a distal end;
a cryospray applicator coupled to the distal end of the mechanical arm, the cryospray applicator comprising an array of orifices, the cryospray applicator moveable by the mechanical arm to deliver a spray of cryogen to a portion of an area of skin tissue for treatment; and
a processor configured to:
receive imagery of a portion of skin of a patient for receiving a skin cooling treatment;
automatically identify boundaries from the received imagery to designate portions of the skin of the patient for receiving the skin cooling treatment;
select at least one potential treatment footprint;
generate a treatment path for the portion of skin of the patient designated for receiving the skin cooling treatment based on the identified boundaries and on the at least one potential treatment footprint;
deliver the skin cooling treatment to the skin according to the treatment path and the at least one potential treatment footprint; and
determine an instantaneous treatment footprint while delivering the skin cooling treatment to the skin according to the treatment path.

2. The system of claim 1, wherein receiving imagery of the portion of skin of the patient comprises generating imagery of the portion of the skin of the patient with a vision system coupled to the cryospray applicator.

3. The system of claim 2, wherein the imagery includes visible spectrum imagery and infrared imagery.

4. The system of claim 1, wherein the processor is further configured to: determine perfusion of the portion of skin designated for receiving the skin cooling treatment; and adjust a dosing according to the perfusion of the portion of skin designated for receiving the skin cooling treatment.

5. The system of claim 1, wherein the processor is further configured to receive temperature information from the treatment footprint and change advancing of the cryospray applicator across the skin according to the temperature information, and wherein delivering the skin cooling treatment comprises advancing the cryospray applicator across the skin of the patient according to the treatment path.

6. The system of claim 5, wherein the temperature information comprises data characterizing an advance of a freezing-front.

7. The system of claim 1, wherein automatically identifying boundaries comprises: identifying a no-go feature; creating a no-go zone comprising the no-go feature and a safety offset at least partially surrounding the no-go feature; and creating boundary delineating between the no-go zone and the portions of skin designated for receiving skin cooling treatment.

8. The system of claim 7, wherein the treatment path prevents treatment in the no-go zone.

9. The system of claim 1, wherein the processor is further configured to: determine a distance between the skin receiving the cooling treatment and the cryospray applicator; and ascertain an attribute of the skin designated for receiving the skin cooling treatment before delivering the skin cooling treatment, wherein the attribute comprises at least one of: a deformation; or a cooling response.

10. The system of claim 9, wherein determining the attribute of the skin comprises: directing a spray at least some of the skin designated for receiving the skin cooling treatment; and measuring a deformation of the at least some of the skin resulting from the directed spray, wherein the deformation comprises a depression; wherein the processor is further configured to modify the delivering of the skin cooling treatment based on the measured deformation of the at least some of the skin resulting from the directed spray.

11. The system of claim 10, wherein the processor is further configured to select a nozzle, and wherein the instantaneous treatment footprint is determined based in part on the selected nozzle.

12. The system of claim 1, wherein the processor is further configured to determine an attribute of the treated skin subsequent to the delivering of the skin cooling treatment, wherein the attribute comprises at least one of: an erythema level; or a re-warming rate.

13. The system of claim 12, wherein the processor is further configured to at least one of: deliver a rewarming treatment based on the determined attribute of the treated skin; or update a patient profile of the patient with information for adjusting a future treatment based on the determined attribute of the treated skin.

14. The system of claim 1, wherein the processor is further configured to: detect a motion of the patient; generate a modified treatment path based on the motion of the patient; and deliver the skin cooling treatment according to the modified treatment path.

15. The system of claim 1, wherein the skin cooling treatment is delivered via the cryospray applicator while moving the cryospray applicator along the treatment path.

16. The system of claim 15, wherein the instantaneous footprint is determined while moving the cryospray applicator along the treatment path.

17. The system of claim 16, wherein the processor is further configured to characterize at least one structure underlying the skin of the patient via a preliminary sweep of the cryospray applicator across at least a portion of skin of the patient for receiving the skin cooling treatment before delivering the skin cooling treatment.

18. The system of claim 1, wherein the processor is further configured to modify the treatment path based on the instantaneous treatment footprint while delivering the skin cooling treatment to the skin.

19. The system of claim 1, wherein the processor is further configured to:
determine to adjust a dosing based on imagery received during the delivering of the skin cooling treatment;
modify the instantaneous treatment footprint while delivering the skin cooling treatment to the skin to affect the dosing modification; and
modify the treatment path while delivering the skin cooling treatment to the skin based on the modified instantaneous treatment footprint.

20. A method of controlling a skin cooling treatment system comprising a mechanical arm having a cryospray applicator coupled to a distal end of the mechanical arm, the method comprising:
receiving imagery of a portion of skin of a patient for receiving a skin cooling treatment;
automatically identifying boundaries from the received imagery to designate portions of the skin of the patient for receiving the skin cooling treatment;
selecting at least one potential treatment footprint;
generating a treatment path for the portion of skin of the patient designated for receiving the skin cooling treatment based on the identified boundaries and on the at least one potential treatment footprint;
delivering the skin cooling treatment to the skin according to the treatment path and the at least one potential treatment footprint; and determining an instantaneous treatment footprint while delivering the skin cooling treatment to the skin according to the treatment path.

21. The method of claim 20, wherein receiving imagery of the portion of skin of the patient comprises generating imagery of the portion of the skin of the patient with a vision system coupled to the cryospray applicator.

22. The method of claim 21, wherein the imagery includes visible spectrum imagery and infrared imagery.

23. The method of claim 20, further comprising:
determining perfusion of the portion of skin designated for receiving the skin cooling treatment; and adjusting a dosing according to the perfusion of the portion of skin designated for receiving the skin cooling treatment.

24. The method of claim 20, further comprising receiving temperature information from the treatment footprint and changing advancing of the cryospray applicator across the skin according to the temperature information, wherein delivering the skin cooling treatment comprises advancing the cryospray applicator across the skin of the patient according to the treatment path.

25. The method of claim 24, wherein the temperature information comprises data characterizing an advance of a freezing-front.

26. The method of claim 20, wherein automatically identifying boundaries comprises: identifying a no-go feature; creating a no-go zone comprising the no-go feature and a safety offset at least partially surrounding the no-go feature; and creating boundary delineating between the no-go zone and the portions of skin designated for receiving skin cooling treatment.

27. The method of claim 26, wherein the treatment path prevents treatment in the no-go zone.

28. The method of claim 20, further comprising:
determining a distance between the skin receiving the cooling treatment and the cryospray applicator; and determining an attribute of the skin designated for receiving the skin cooling treatment before delivering the skin cooling treatment; wherein the attribute comprises at least one of: a deformation; or a cooling response.

29. The method of claim 28, wherein determining the attribute of the skin comprises: directing a spray at least some of the skin designated for receiving the skin cooling treatment; and measuring a deformation of the at least some of the skin resulting from the directed spray; the method further comprising modifying the delivering of the skin cooling treatment based on the measured deformation of the at least some of the skin resulting from the directed spray.

30. The method of claim 29, further comprising selecting a nozzle, and wherein the instantaneous treatment footprint is determined based on the selected nozzle.

31. The method of claim 20, further comprising:
determining an attribute of the treated skin subsequent to the delivering of the skin cooling treatment, wherein the attribute comprises at least one of: an erythema level; or a re-warming rate; and at least one of: delivering a rewarming treatment based on the determined attribute of the treated skin; or updating a patient profile of the patient with information for adjusting a future treatment based on the determined attribute of the treated skin.

32. The method of claim 20, further comprising:
detecting a motion of the patient; generating a modified treatment path based on the motion of the patient; and delivering the skin cooling treatment according to the modified treatment path.

33. The method of claim 20, wherein the skin cooling treatment is delivered via the cryospray applicator while moving the cryospray applicator along the treatment path.

34. The method of claim 33, wherein the instantaneous footprint is determined while moving the cryospray applicator along the treatment path.

35. The method of claim 34, further comprising characterizing at least one structure underlying the skin of the patient via a preliminary sweep of the cryospray applicator across at least a portion of skin of the patient for receiving the skin cooling treatment before delivering the skin cooling treatment.

36. The method of claim 20, further comprising modifying the treatment path based on the instantaneous treatment footprint while delivering the skin cooling treatment to the skin.

37. The method of claim 20, further comprising:
determining to adjust a dosing based on imagery received during the delivering of the skin cooling treatment;
modifying the instantaneous treatment footprint while delivering the skin cooling treatment to the skin to affect the dosing modification; and
modifying the treatment path while delivering the skin cooling treatment to the skin based on the modified instantaneous treatment footprint.

* * * * *